US008880181B2

(12) United States Patent
Chambers

(10) Patent No.: US 8,880,181 B2
(45) **Date of Patent: *Nov. 4, 2014**

(54) IMPLANTABLE ELECTRICAL CONNECTOR HAVING UNITARY CONTACTS

(75) Inventor: John Chambers, Mona Vale (AU)

(73) Assignee: Cochlear Limited, Macquarie University, NSW (AU)

( * ) Notice: Subject to any disclaimer, the term of this patent is extended or adjusted under 35 U.S.C. 154(b) by 811 days.

This patent is subject to a terminal disclaimer.

(21) Appl. No.: 12/771,644

(22) Filed: Apr. 30, 2010

(65) Prior Publication Data

US 2011/0270355 A1 Nov. 3, 2011

(51) Int. Cl.

| | |
|---|---|
| ***A61N 1/375*** | (2006.01) |
| ***H01R 4/02*** | (2006.01) |
| ***H01R 24/58*** | (2011.01) |
| *A61N 1/36* | (2006.01) |
| *H01R 107/00* | (2006.01) |

(52) U.S. Cl.

CPC ............ *H01R 4/029* (2013.01); *A61N 1/36032* (2013.01); *H01R 2201/12* (2013.01); *H01R 2107/00* (2013.01); *H01R 24/58* (2013.01)

USPC ............................ 607/57; 607/36; 439/733.1

(58) Field of Classification Search

USPC ................ 607/57, 36, 37, 38; 439/371, 733.1

See application file for complete search history.

(56) References Cited

U.S. PATENT DOCUMENTS

| | | | | |
|---|---|---|---|---|
| 3,941,444 | A | 3/1976 | Bruni et al. | |
| 4,017,139 | A | 4/1977 | Nelson | |
| 4,126,126 | A | 11/1978 | Bare et al. | |
| 4,179,180 | A | 12/1979 | Hanna | |
| 6,129,747 | A | 10/2000 | Lindegren | |
| 7,299,095 | B1 | 11/2007 | Barlow et al. | |
| 7,316,154 | B1 | 1/2008 | Bennett | |
| 7,844,329 | B2 * | 11/2010 | Chambers | 607/2 |
| 2005/0038476 | A1 | 2/2005 | Brown | |
| 2009/0215296 | A1 * | 8/2009 | Chambers | 439/271 |

* cited by examiner

*Primary Examiner* — Alyssa M Alter

(57) ABSTRACT

A connector for electrically connecting implantable components. The connector comprises first and second connector halves configured to be electrically coupled to first and second components, respectively, and one or more readily severable unitary contacts electrically connecting the first and second connector halves to one another.

24 Claims, 23 Drawing Sheets

IMPLANTABLE ELECTRICAL CONNECTOR HAVING UNITARY CONTACTS

BACKGROUND

1. Field of the Invention

The present invention relates generally to electrical connectors, and more particularly, to an implantable electrical connector having unitary contacts.

2. Related Art

Medical devices having one or more implantable components have provided a wide range of therapeutic benefits to patients (sometimes referred to herein as a recipient) over recent decades. One type of implantable medical device that has provided substantial benefits to recipients is the prosthetic hearing device. Prosthetic hearing devices process ambient sound to supplement or provide hearing ability to a hearing impaired recipient.

Prosthetic hearing devices include a category of implantable devices known as cochlear implants (also referred to as cochlear devices, cochlear implant devices, and the like; "cochlear implants" herein). Cochlear implants include one or more implanted in, or worn by the recipient to receive ambient sound. A sound processor processes the ambient sound received by the microphone(s).

Cochlear implants also include an array of stimulation electrodes disposed on the distal end of an elongate electrode assembly which is implanted in the cochlea of the patient (sometimes referred to herein as a recipient). The electrode array is controlled by stimulator unit encased in a hermetically sealed, biocompatible housing which is typically implanted in the mastoid. The stimulator unit, which is responsive to the sound processor, essentially contains decoder and driver circuits for the stimulation electrodes.

In cochlear implants, the stimulator unit may require replacement or adjustment for various reasons, such as device failure, infection, replacement or replenishment of batteries or other energy storage systems, etc. However, in current cochlear implants, the permanent wiring between the electrode assembly and the stimulator unit make the removal and re-attachment of the stimulator unit impracticable. Such arrangements are problematic because removal of the stimulator unit causes disturbance of the electrode assembly that may result in damage to the delicate structures of the cochlea or other body tissue.

SUMMARY

In one aspect of the present invention, a medical device is provided. The medical device comprises first and second implantable components; an electrical connector configured to electrically connect the first and second components, comprising: first and second connector halves electrically coupled to the first and second components, respectively, and one or more readily severable unitary contacts electrically connecting the first and second connector halves to one another.

In another aspect of the present invention, a connector for electrically connecting first and second implantable components is provided. The connector comprises first and second connector halves configured to be electrically coupled to the first and second components, respectively, and one or more readily severable unitary contacts electrically connecting the first and second connector halves to one another.

In a still other aspect of the present invention, a method of manufacturing a connector for electrically connecting first and second implantable components is provided. The method comprises: providing first and second connector halves; and forming at least one readily severable unitary contact between the first and second connector halves.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to an electrical connector that electrically connects two implantable components of, for example, an implantable medical device. The electrical connector comprises two mating halves each electrically coupled to one of the two implantable components. When the connector halves are physically engaged with, and electrically connected to, one another (referred to as "mated" herein, regardless of the connector configuration), the halves are electrically connected to one another by a plurality of unitary contacts. A unitary contact is a contiguous conductive pathway which extends between the mated connector halves, and which is substantially free of surface boundaries. As used herein, a surface boundary is a site at which two conductive elements physically abut and create a discontinuity there between.

In embodiments of the present invention the contiguous unitary contacts are configured to be readily severable. That is, the contiguous unitary contacts are configured to be severed or broken through the application of a minimal amount of manual force. As used herein, a minimal amount of force refers to a force that is easily and manually applied, in vivo, by a surgeon. However, the minimal amount of force required to sever one or more unitary contacts is great enough that the contacts will not sever as a result of forces applied during normal in vivo usage of the connector. In embodiments in which the electrical connector connects a first component with an implanted component, this minimal force is below a level that substantially disturbs the location of the implanted component. This permits in situ physical separation of the connector halves and thus he separation of the components without causing translation, rotation or otherwise physically disturbing the implanted component. As used herein, in situ operations, such as the separation, adjustment and/or replacement of components, is an operation performed while one or more components are implanted in a recipient.

Exemplary embodiments of the present invention are described herein with reference to one type of implantable medical device, a prosthetic hearing device, namely, a cochlear implant. It would be appreciated that an electrical connector in accordance with embodiments of the present invention may be used in other implantable devices. For example, implantable devices in which embodiments of the present invention may be implemented include, but are limited to, implantable medical devices such as neural stimulators, pacemakers, fluid pumps, sensors, drug delivery systems, etc.

It would also be appreciated that an electrical connector in accordance with embodiments of the present invention may be used to connect a variety of different components. For example, in one exemplary application, embodiments of the connector of the present invention may be used to connect an auxiliary power source to an implanted component.

Figure 1:
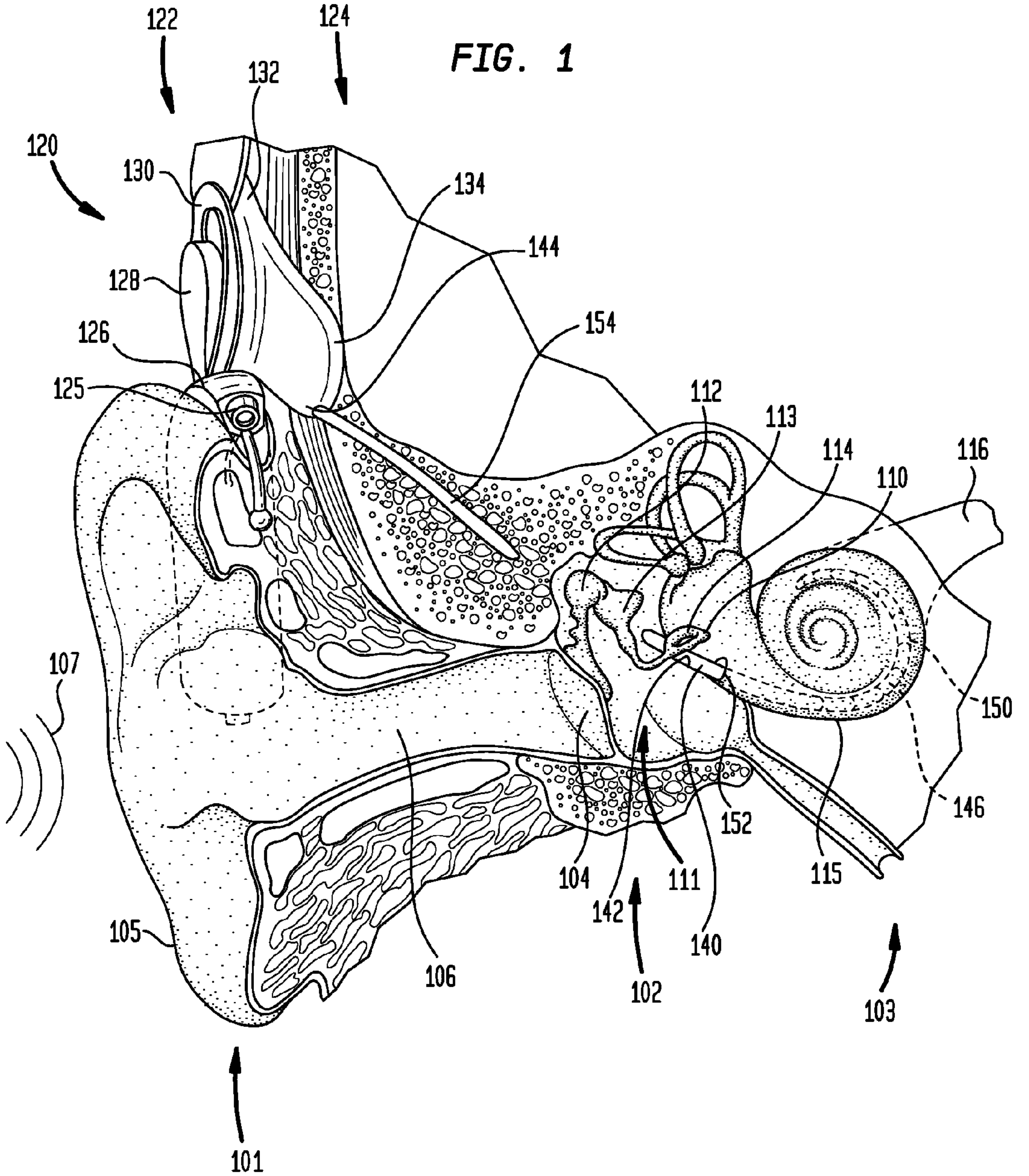
FIG. 1 is a perspective view of an exemplary implantable medical device, namely a cochlear implant implanted in a recipient, in which embodiments of the present invention may be advantageously implemented.

FIG. 1 illustrates an exemplary cochlear implant in which aspects of the present invention may be implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In certain profoundly deaf persons, there is an absence or destruction of the hair cells. Cochlear implants, such a cochlear implant 120, are utilized to directly stimulate the ganglion cells to provide a hearing sensation to the recipient.

FIG. 1 also illustrates the positioning of cochlear implant 120 relative to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is output to a behind-the-ear (BTE) speech processing unit 126 that generates coded signals which are provided to an external transmitter unit 128, along with power from a power source (not shown) such as a battery. External transmitter unit 128 comprises an external coil 130 and, preferably, a magnet (not shown) secured directly or indirectly in external coil 130.

In the cochlear implant embodiment illustrated in FIG. 1, internal component assembly 124 comprises an internal coil 132 of a stimulator unit 134 that receives and transmits power and coded signals received from external assembly 122 to other elements of stimulator unit 134 which apply the coded signal to cochlea 115 via an implanted electrode assembly 140. Connected to stimulator unit 134 is a flexible cable 154. Flexible cable 154 electrically couples stimulator unit 134 to electrode assembly 140. Electrode assembly 140 comprises a carrier member 142 having one or more electrodes 150 positioned on an electrode array 146. Electrode assembly 140 enters cochlea 115 at cochleostomy region 152 and is positioned such that electrodes 150 are substantially aligned with portions of tonotopically-mapped cochlea 115. Signals generated by stimulator unit 134 are typically applied by the array 146 of electrodes 150 to cochlea 115, thereby stimulating auditory nerve 116.

Although embodiments of the present invention are described herein with reference to a cochlear implant 120 having external and internal components, it would appreciated that embodiments of the present invention may also be implemented in a totally implantable cochlear implant. In such totally implantable devices, the sound processor and/or the microphone may be implanted in the recipient. Such totally implantable devices are described in, for example, H. P. Zenner et al. "First implantations of a totally implantable electronic hearing system for sensorineural hearing loss", in HNO Vol. 46, 1998, pp. 844-852; H. Leysieffer et al. "A totally implantable hearing device for the treatment of sensorineural hearing loss: TICA LZ 3001", in HNO Vol. 46, 1998, pp. 853-863; and H. P. Zenner et al. "Totally implantable hearing device for sensorineural hearing loss", in The Lancet Vol. 352, No. 9142, page 1751, the contents of which are hereby incorporated by reference herein.

Figure 2A:
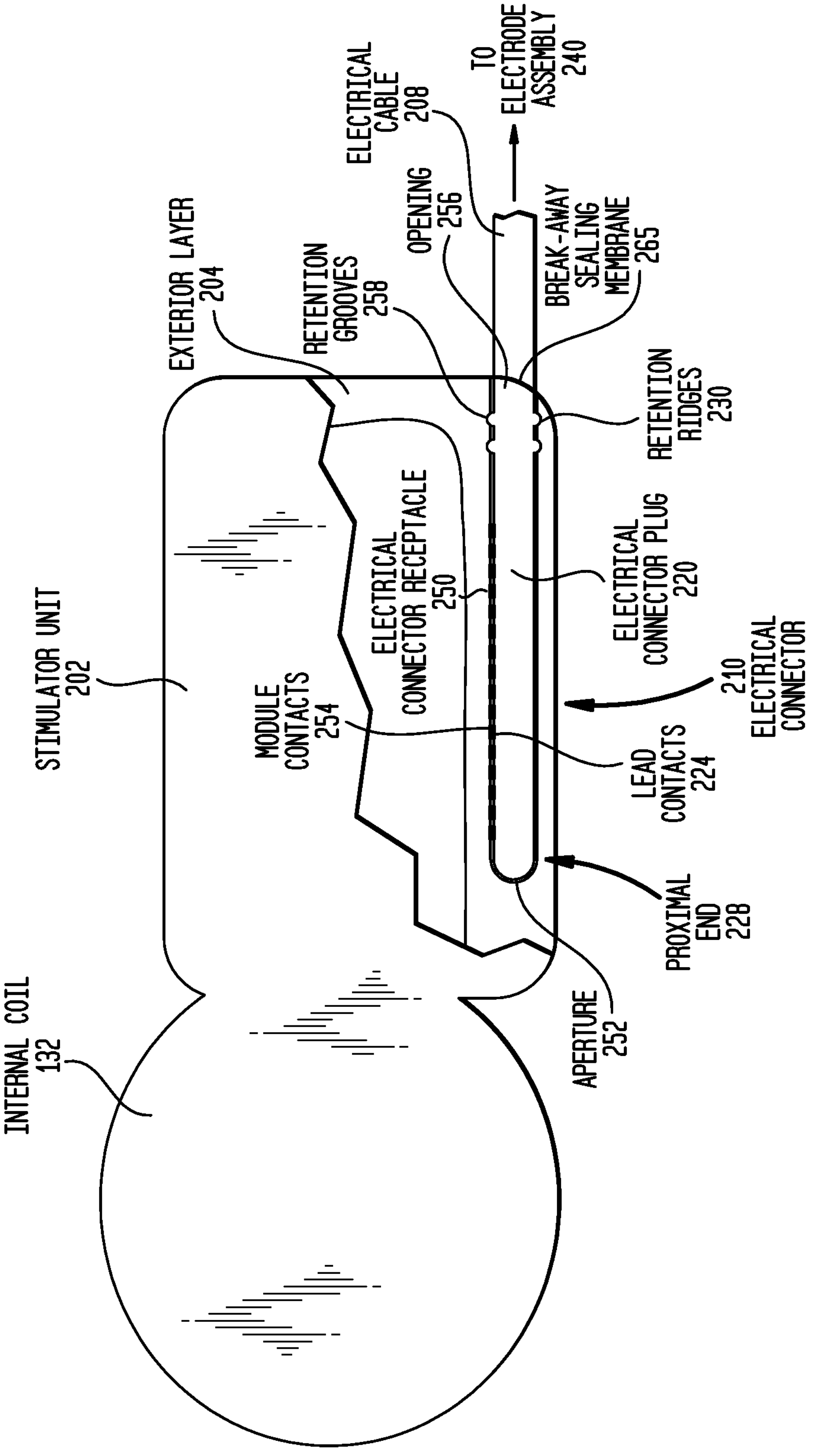
FIG. 2A is a side view of the stimulator unit depicted in FIG. 1 partially broken away to illustrate the electrical connection of the stimulator unit and the electrode assembly of FIG. 1 via an embodiment of the electrical connector of the present invention.

FIGS. 2A-2E illustrate a first embodiment of an electrical connector of the present invention. As shown in FIG. 2A, a stimulator unit 202, which is an embodiment of stimulator 134 of FIG. 1, and generates stimulation signals in response to signals generated by the sound processor (not shown) as described above with reference to FIG. 1. These stimulation signals are transmitted to an electrode assembly 240 (FIG. 2B) via electrical connector 210. Electrode assembly 240 comprises an embodiment of electrode assembly of FIG. 1 and, as described above with reference to FIG. 1, delivers the stimulation signals to the cochlea of the recipient.

In the embodiment of FIG. 2A, electrical connector 210 comprises two connector halves. A first connector half, is an electrical connector receptacle 250 which is electrically coupled to stimulator unit 202. Electrical connector receptacle 250 is sometimes referred to herein as a module connector half. A second connector half is an electrical connector plug 220 which is electrically coupled to electrode assembly 240. Electrical connector plug 220 is sometimes referred to herein as a lead connector half. Electrical connector plug 220 is mated with electrical connector receptacle 250 by inserting connector plug 220 into electrical connector receptacle 250.

As shown, electrical connector 210 may be sealed to maintain the integrity of the electrical connection between electrical connector receptacle 250 and electrical connector plug 220 while the connector halves are mated. The seal is provided by a break-away sealing membrane 265 that prevents the ingress of fluid that would jeopardize the electrical connection between electrical connector receptacle 250 and electrical connector plug 220. Break-away sealing membrane 265 is configured to be ruptured when the connector halves are disconnected from each other using minimal force. In certain circumstances, the rupture in break-away sealing membrane 265 may result from the manual application of a force, for example, via a medical instrument such as a scalpel. In other embodiments, break-away sealing membrane 265 may be ruptured by exerting a minimal rotational, translational, or other force on electrical cable 208 or electrical connector plug 220. In these embodiments, a surgeon may slightly twist, pull, or otherwise move electrical cable 208 or electrical connector plug 220 so as to cause break-away sealing membrane 265 to rupture. It should be appreciated that break-away sealing membrane 265 may be configured to rupture as a result of various other forces or mechanisms.

It would be appreciated that break-away sealing membrane 265 may comprise polyurethane, parylene, silicone elastomer, or any other biocompatible material that is substantially resistant to the ingress of biological fluids. It would also be appreciated that a variety of coating techniques may be used to apply break-away sealing membrane 265. For example, break-away sealing membrane 265 may be applied by dipping the mated connector halves into a tank of liquid biocompatible material, spraying the biocompatible material on electrical connector 210, or manually applying an epoxy or other surface sealant. It should be appreciated that any other process for applying a material may also be used to apply break-away sealing membrane 265.

As shown in FIG. 2A, an exterior layer 204 is provided on the surface of stimulator 202. For ease of illustration, exterior layer 204 has been shown partially removed in FIG. 2A. Similar to break-away sealing membrane 265, exterior layer 204 may comprise a biocompatible material configured to seal stimulator unit 202, and may comprise silicone, parylene, silicone elastomer, or other biocompatible material. Exterior layer 204 may be applied via any of the coating processes described above with reference to the application of break-away sealing membrane 265. In certain embodiments, exterior layer 204 may comprise a hermetic sealing layer.

As described below with reference to FIG. 2C, in certain embodiments, electrical connector receptacle 250 is integrated within exterior layer 204. In these embodiments, electrical connector receptacle 250 is electrically coupled to stimulator unit 202 via wires extending through exterior layer 204.

In the embodiment illustrated in FIG. 2A, flexible electrical cable 208 is provided to electrically couple electrical connector plug 220 to electrode assembly 240. Flexible cable 208 assists in the physical separation of stimulator unit 202 from electrode assembly 240 without causing translation, rotation or otherwise physically disturbing electrode assembly 240 implanted in the cochlea of the recipient. In such embodiments, following the rupture of break-away sealing membrane 265, electrical connector plug 220 may be moved or repositioned without disturbing the position of electrode assembly 240.

Figure 2B:
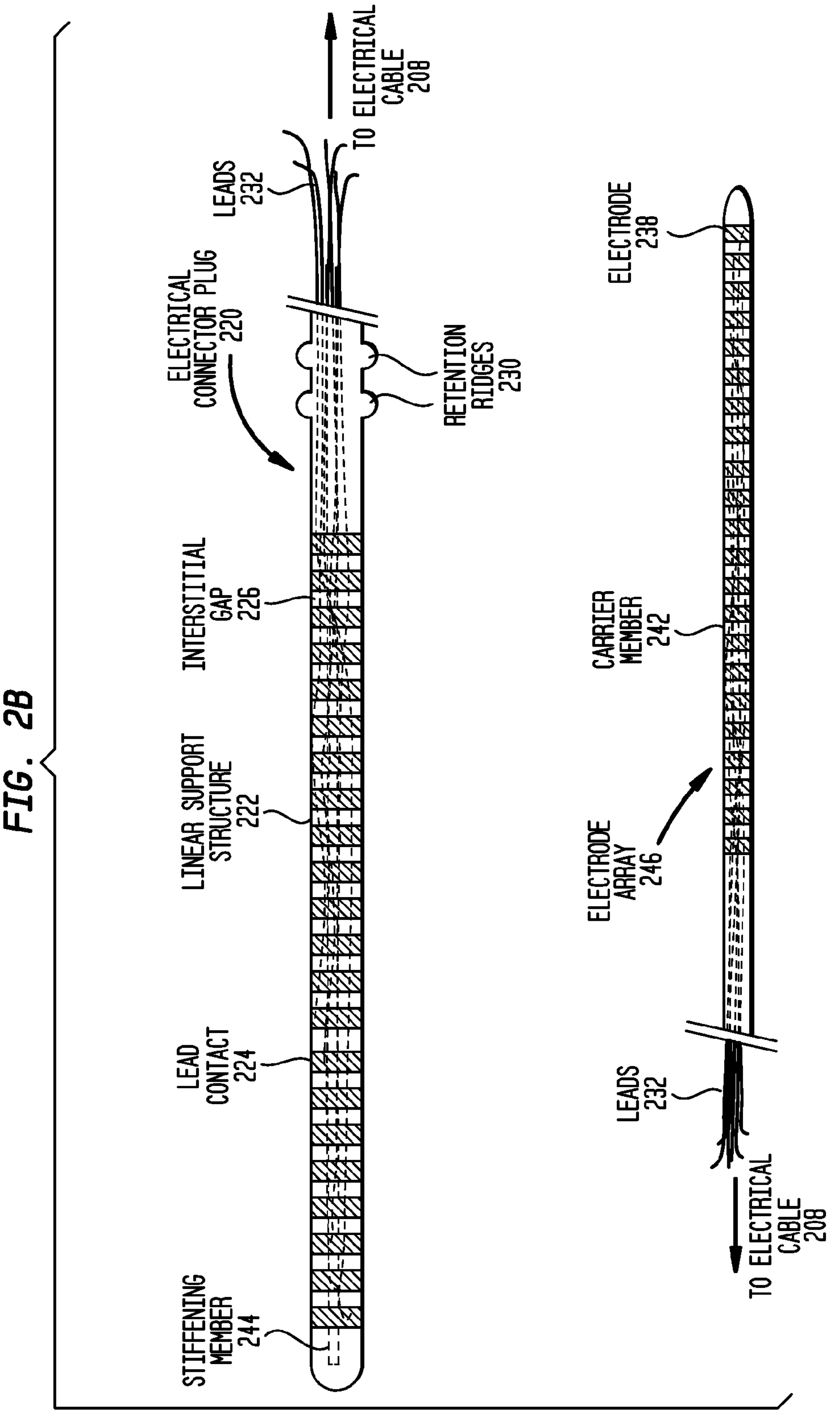
FIG. 2B is a side view of the electrode assembly depicted in FIG. 2A broken away to illustrate an embodiment of the electrical connector plug of the electrical connector illustrated in FIG. 2A.

FIG. 2B is a side view of electrical connector plug 220 of FIG. 2A and electrode assembly 240. For ease of illustration, electrical connector plug 220 and electrode assembly 240 have been shown separated. As described above with reference to FIG. 1, electrode assembly 240 comprises a flexible carrier member 242 having an array 246 of electrodes 238 to deliver stimulation signals to the cochlea of the recipient.

Carrier member 242 may comprise a resiliently flexible material or combination of materials, which curl or are capable of being curled in a manner which follows the curvature of the recipient's cochlea 115.

In the embodiment illustrated in FIG. 2B, electrical connector plug 220 comprises a substantially straight elongate member, referred to as linear support structure 222. Disposed in or on linear support structure 222 is a plurality of lead contacts 224 separated by interstitial gaps 226. Interstitial gaps 226 comprise insulating portions of linear support structure 222 that electrically insulate lead contacts 224 from one another.

Further illustrated in FIG. 2B are leads 232 which extend from electrodes 238 through electrical cable 208 to lead contacts 224. Electrical cable 208 may comprise a flexible material having one or more lumens through which leads 232 extend through. In certain embodiments, electrical cable 208 may comprise a resiliently flexible material or combination of materials configured to adopt a desired or predetermined configuration.

Electrical connector plug 220 may further comprise an elongate stiffening member 244 positioned in linear support structure 222. Elongate stiffening member 244 provides electrical connector plug 220 with sufficient rigidity to permit insertion and/or removal of electrical connector plug 220 into/from electrical connector receptacle 250 with a minimal amount of force. Stiffening member 244 may comprise a surgical grade stainless steel or titanium member substantially extending the length of linear support structure 222. However, it would be appreciated that stiffening member 244 may comprise any suitable shape or material that provides electrical connector plug 220 with rigidity. Furthermore, it should be appreciated that linear support structure 222 may comprise an at least partially rigid material capable of permitting the insertion and removal of electrical connector plug 220 into/from electrical connector receptacle 250 without the need for stiffening member 244.

Figure 2C:
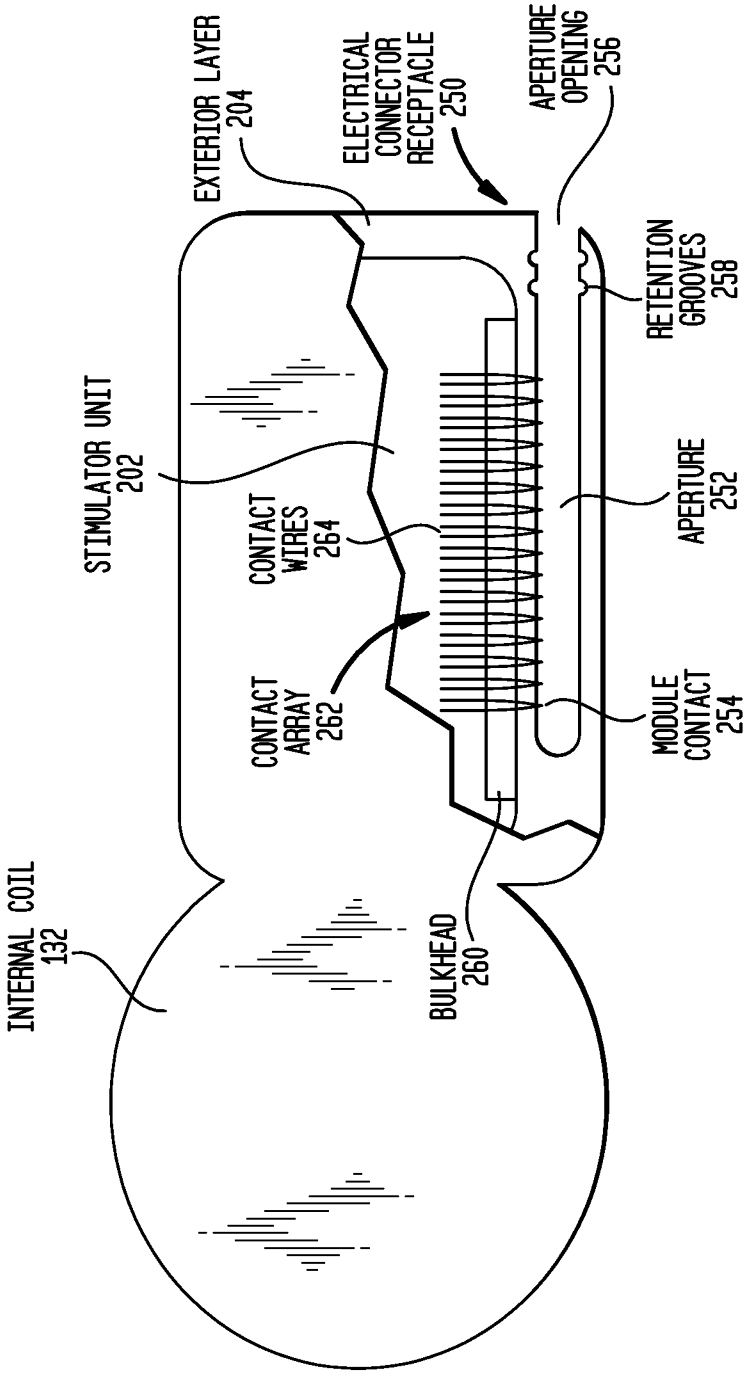
FIG. 2C is a side view of the stimulator unit depicted in FIG. 2A broken away to illustrate an embodiment of the electrical connector receptacle of the electrical connector illustrated in FIG. 2A.

As shown in FIG. 2C, electrical connector receptacle 250 is located in exterior layer 204 and electrical connector plug 220 is inserted into electrical connector receptacle 250. Electrical connector receptacle 250 comprises aperture 252, having an aperture opening 256. In the illustrated embodiment, aperture 252 has a substantially circular cross-section extending the elongate length of aperture 252.

Electrical connector receptacle 250 is electrically coupled to stimulator unit 202 via an array 262 of contact wires 264 extending through exterior layer 204. Module contacts 254 are each connected to one or more contact wires 264. Contact wires 264 extend from module contacts 254 through bulkhead 260 to other components of stimulator unit 202. Contact wires 264 carry electrical signals, such as stimulation signals, between components of stimulator unit 202 and module contacts 254. Connections between two or more contacts wires 264, or between contacts wires 264 and module contacts 254, may be provided by metal-to-metal welds. Details of the formation of exemplary metal-to-metal welds are provided below.

As noted above, in the embodiment illustrated in FIG. 2C, contact wires 264 extend through bulkhead 260. Bulkhead 260 may be configured to provide structural support for contact wires 264, thereby increasing the durability of contact array 262. Bulkhead 260 may further comprise an insulating material so as to electrically isolate contact wires from one another.

Figure 2D:
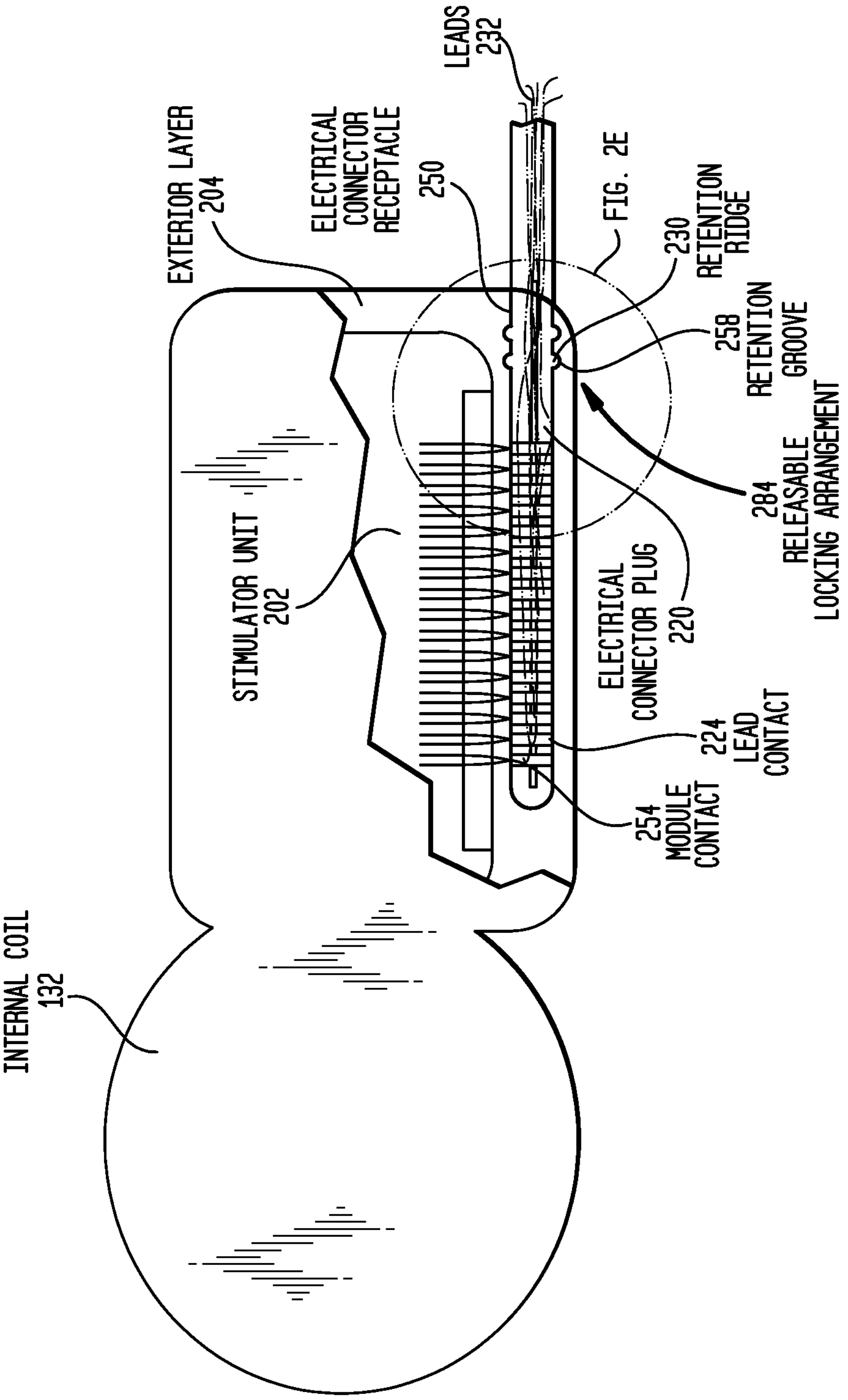
FIG. 2D is a side view of the stimulator unit illustrated in FIG. 2A broken away to illustrate the mated arrangement of the electrical connector plug of FIG. 2B and the electrical connector receptacle of FIG. 2C, in accordance with embodiments of the present invention.

FIG. 2D is cut-away, side view of stimulator unit 202 having electrical connector plug 220 mated with electrical connector receptacle 250. As shown, lead contacts 224 are configured to be electrically coupled to corresponding module contacts 254 of electrical connector receptacle 250. That is, when electrical connector plug 220 is positioned in electrical connector receptacle 250, each lead contact 224 is aligned with a corresponding module contact 254 to form a physical connection there between. This physical connection provides an electrically conductive pathway between each lead contact 224 and module contact 254 so as to electrically couple stimulator unit 202 and electrode assembly 240.

Plug 220 further comprises retention ridges 230 which are configured to engage retention grooves 258 of receptacle 250. When engaged with one another, retention ridges 230 and retention grooves 258 cooperate to releasably retain electrical connector plug 220 in position with respect to electrical connector receptacle 250. Retention ridges 230 are configured to engage, and be removed from, retention grooves 258 with a minimal amount of rotational and/or translational force. As such, retention ridges 230 may comprise a readily deformable material.

As shown in FIG. 2D, retention ridges 230 comprise two pairs of discrete convex structures positioned on opposite sides of linear support structure 222. Similarly, retention grooves 258 comprise two pairs of discrete concave structures, each configured to receive one of the convex shaped retention ridges 230. Although FIG. 2D illustrates releasable locking arrangement 284 comprising two pairs of each of retention ridges 230 and retention grooves 258, it would be appreciated that locking arrangement 284 may comprise more or less pairs of retention ridges 230 and retention grooves 258.

Figure 2E:
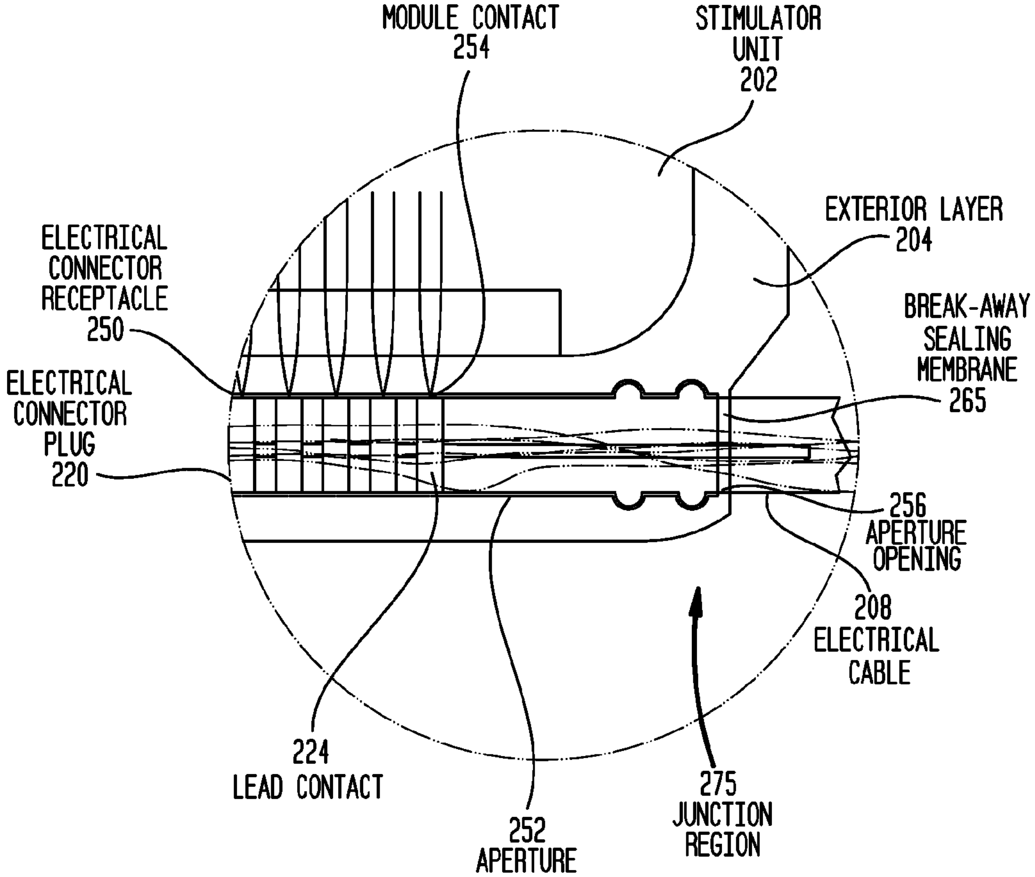
FIG. 2E is an enlarged view of a portion of the mated arrangement of the electrical connector plug and the electrical connector receptacle of FIG. 2D.

FIG. 2E is an enlarged view of the area of FIG. 2D bounded by a dashed circle and labeled as FIG. 2E. As described above, when electrical connector plug 220 is inserted into electrical connector receptacle 250, an electrical connection is created between stimulator unit 202 and electrodes 238. Also as noted above, a break-away sealing membrane 265 is provided that prevents fluids from substantially interfering with the electrical connections between lead contacts 224 and module contacts 254.

Although break-away sealing membrane 265 has been discussed thus far as a sealing element that is separate from exterior layer 204, it should be appreciated that break-away sealing membrane 265 may comprise a portion of exterior layer 204. For example, break-away sealing membrane 265 may comprise a portion of exterior layer 204 having a thickness that is substantially less than the remainder of exterior layer 204.

In an alternative arrangement, exterior layer 204 may comprise first and second materials, each material having different rupture strengths. As used herein, rupture strength refers to the ability of a material to withstand the application of a force before rupturing. A difference in rupture strength may also be provided by using different grades of a material. For example, a first material having greater rupture strength is configured to substantially cover stimulator unit 202, while break-away membrane 265 comprises a second material having lower rupture strength. In such applications, the first material is configured to remain intact upon the application of a force to break-away sealing membrane 265.

In another configuration, break-away sealing membrane 265 may comprise a portion of exterior layer 204 that is substantially surrounded by, or is adjacent to, a mechanical weakness such that the application of a minimal force to the break-away sealing membrane results in a rupture occurring at the mechanical weakness. An exemplary mechanical weakness in exterior layer 204 may comprise a score, notch, or any other intentionally created weakness that permits ready rupturing, yet is capable of maintaining the integrity of the seal prior to application of the minimal force. It would be appreciated that a mechanical weakness may be utilized when break-away sealing membrane 265 comprises a sealing element that is separate from exterior layer 204.

Exterior layer 204 may include a rupture-limiting arrangement configured to prevent any rupture in break-away sealing membrane 265 from spreading to the remainder of exterior layer 204. An exemplary rupture-limiting arrangement may comprise one or more implanted members adjacent to, or substantially surrounding, break-away sealing membrane 265. For example, such a rupture-limiting arrangement may be provided by including metal members within outer coating 204 that act as internal cutting members upon the application of a force to break-away sealing membrane 265. In a specific configuration, a pair of adjacent yet physically spaced metal members, each having a sharp portion, is disposed in exterior layer 204. Upon application of a force, the sharp portions of the spaced members cause any rupture to occur substantially between the metal members.

As shown in FIGS. 2A-2E, electrical connector receptacle 250 is located in exterior layer 204, and break-away sealing membrane 265 is integrated with, or positioned on, the surface of exterior layer 204 circumferentially around electrical connector plug 220 at opening 256. However, as noted above, electrical connector receptacle 250 is not necessarily located in exterior layer 204 and electrical connector receptacle 250 and stimulator unit 202 may be located in physically separate housings.

In the embodiments of FIGS. 2A-2E, electrical connector receptacle 250 and electrical connector plug 220 are configured to provide a minimum leakage volume there between. That is, electrical connector receptacle 250 and electrical connector plug 220 are designed such that if a fluid penetrates break-away sealing membrane 265, the space between the connector halves is sufficiently small that the fluid will not interfere with the electrical connection between contacts 224, 254. In certain arrangements, at least one of electrical connector receptacle 250 and electrical connector plug 220 comprises a gap consuming compliant material configured to substantially fill any space between electrical connector receptacle 250 and electrical connector plug 220, thereby providing the minimum leakage volume.

Figure 3:
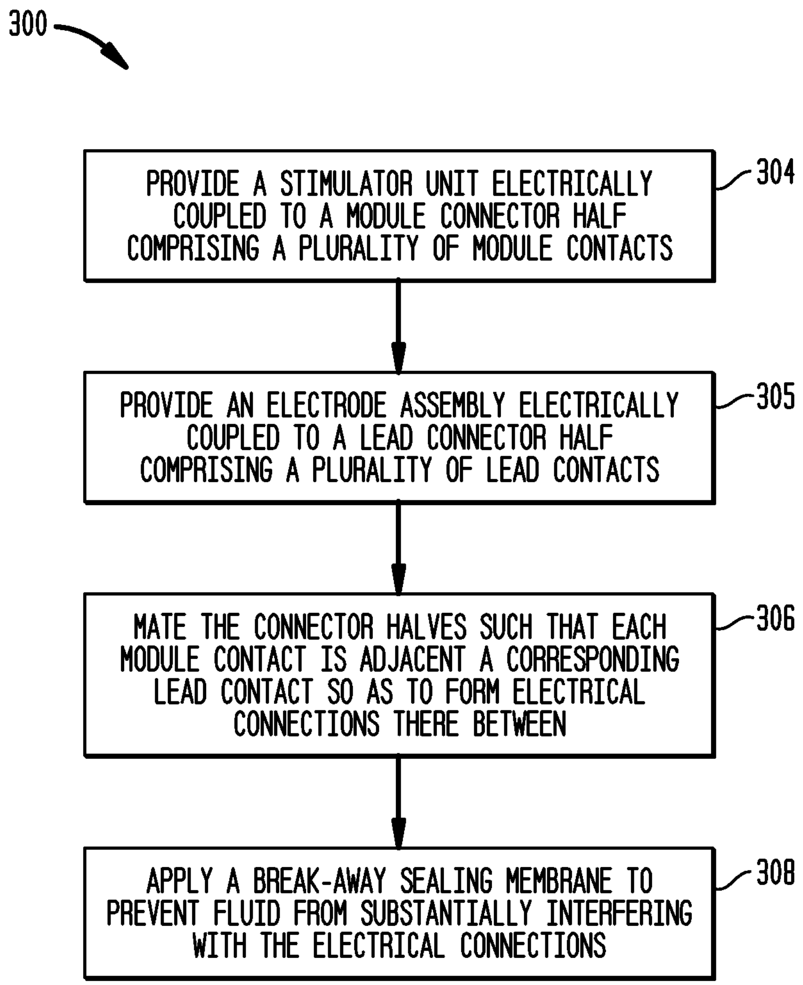
FIG. 3 is a flowchart illustrating the relevant operations performed to electrically connect a stimulator unit and an electrode assembly with an electrical connector, in accordance with embodiments of the present invention.

FIG. 3 is a flowchart illustrating the relevant operations performed to form a releasable, substantially hermetically sealed electrical connection between a stimulator unit and an electrode assembly of a cochlear implant in accordance with embodiments of the present invention. As shown, the illustrative process 300 begins block 304 where a stimulator unit is provided. The stimulator unit is electrically coupled to a module connector half comprising a plurality of module contacts. At block 305, an electrode assembly electrically coupled to a lead connector half is provided. The lead connector half comprises a plurality of lead contacts.

At block 306, the module and lead connector halves are mated with one another such that each module contact is adjacent a corresponding lead contact so as to form electrical connections between the contacts. Thus, upon the mating of the two connector halves, an electrical connection is provided between the stimulator unit and the electrode assembly. After mating of the connector halves, at block 308 a break-away sealing membrane is applied to prevent fluid from substantially interfering with the electrical connections between the contacts. As described above, the break-away sealing membrane may be applied via a coating process.

Figure 4:
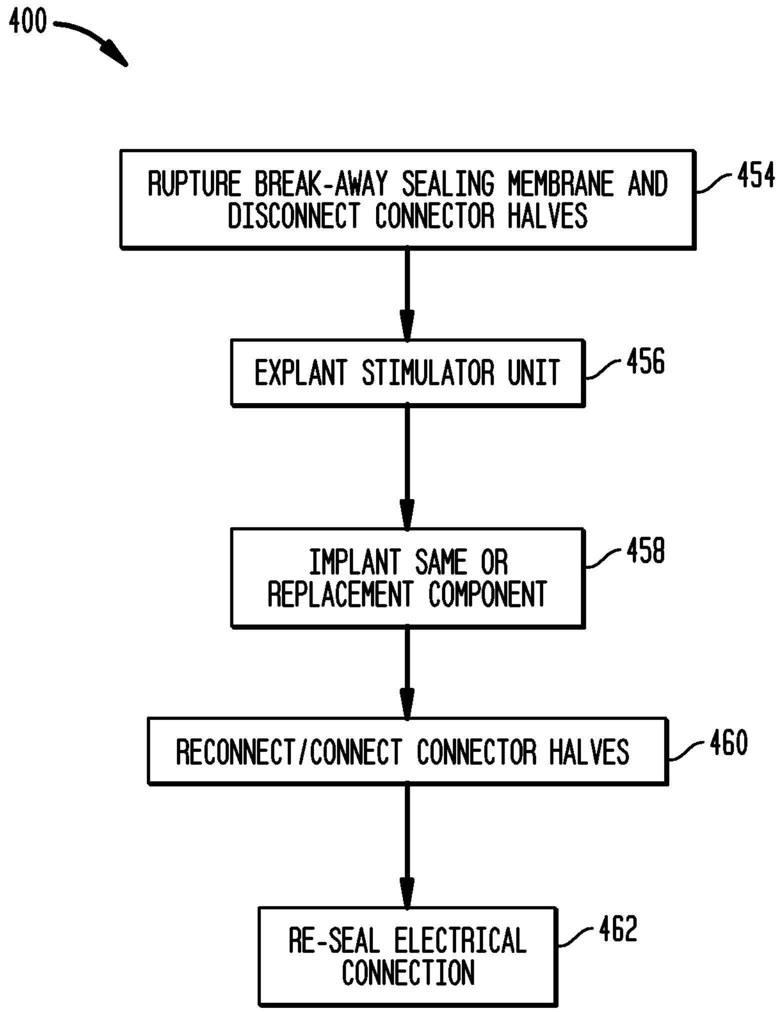
FIG. 4 is a flowchart illustrating the relevant operations performed during in situ replacement of a stimulator unit, in accordance with embodiments of the present invention.

FIG. 4 is a flowchart illustrating the relevant operations performed during the in situ adjustment of an implanted stimulator electrically coupled to an electrode assembly via an electrical connector in accordance with embodiments of the present invention. The stimulator unit is electrically coupled to a module connector half while the electrode assembly electrically coupled to a lead connector half. As used herein, the adjustment of a component, such as a stimulator, refers to the modification or the replacement of the component. The operations of process 400 begin by opening the site of the implanted components and disconnecting the connector halves from one another at block 454. More specifically, the surgeon applies a slight amount of force that ruptures break-away sealing membrane physically separates the connector halves from one another. Once the connector halves have been physically separated, the stimulator unit may be explanted from the recipient at block 456 without physically disturbing the implanted electrode assembly.

At block 458, the explanted stimulator unit, or a replacement stimulator unit, is implanted in the recipient. In embodiments in which a replacement stimulator unit is to be implanted, the replacement stimulator unit would be electrically coupled to a module connector half configured to mate with the lead connector half coupled to the implanted electrode assembly. At block 460, the newly implanted stimulator unit is electrically connected to the electrode assembly by mating the lead and module connector halves. Following connection of the two halves of the electrical connector, the rupture in the break-away sealing membrane may be re-sealed at block 462.

Various processes may be used to reseal the rupture in the break-away sealing membrane. For example, a partially set sealing material may be manually applied to seal the rupture. Alternatively, a fast curing sealing material, such as an ultraviolet light curable biocompatible polymer, may be brushed or sprayed onto the break-away sealing membrane to reseal the rupture. In other circumstances, a manually applied epoxy or other surface sealant may be used to reseal the rupture. In still other embodiments, a pre-set material overlay may be affixed over the rupture via a biocompatible adhesive, thereby sealing the rupture. In such embodiments, the overlay may be a pre-configured element or may be cut or trimmed to size by the surgeon. In other circumstances a new break-away sealing membrane may be provided using the same or similar processes described.

Figure 5A:
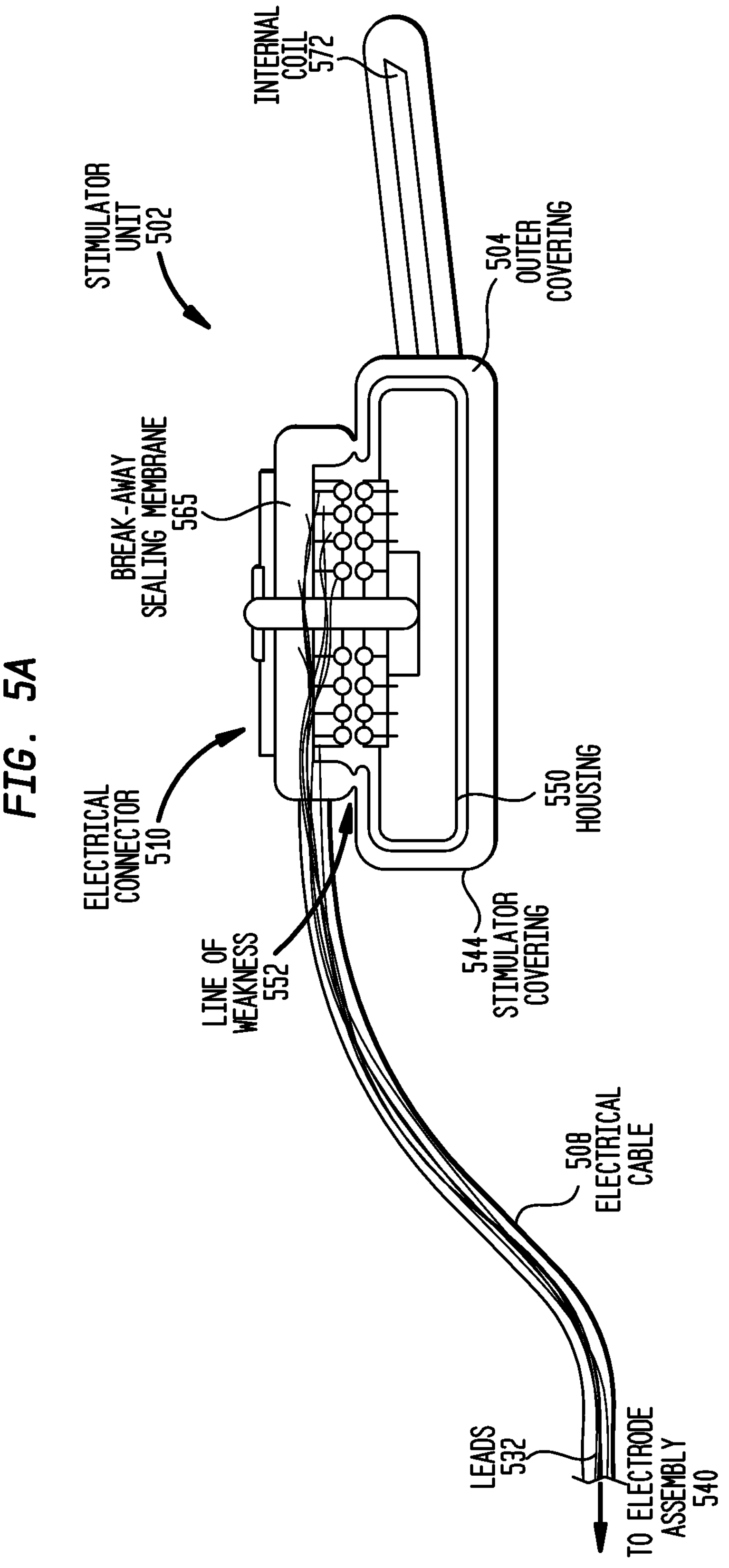
FIG. 5A is cross-sectional side view of the stimulator unit depicted in FIG. 1 electrically connected to an electrode assembly via an electrical connector, in accordance with embodiments of the present invention.

FIG. 5A illustrates a perspective view of an alternative electrical connector. Illustrated in FIG. 5A is an embodiment of stimulator unit 134, referred to as stimulator unit 502. Stimulator unit 502 comprises a housing 550 having substantially the same components there as stimulator unit 134 of FIG. 1. Housing 550 is sealed by a biocompatible exterior layer 504 that is substantially similar to exterior layer 204 of FIGS. 2A-2E. Connected to stimulator unit 502 is internal coil 572 which is similar to internal coil 132 of FIG. 1. In the embodiments of FIG. 5A, an electrode assembly 540 (not shown) is electrically connected to stimulator unit 502 via an electrical connector 510. Details of electrical connector 510 are described below with reference to FIG. 5B.

Figure 5B:
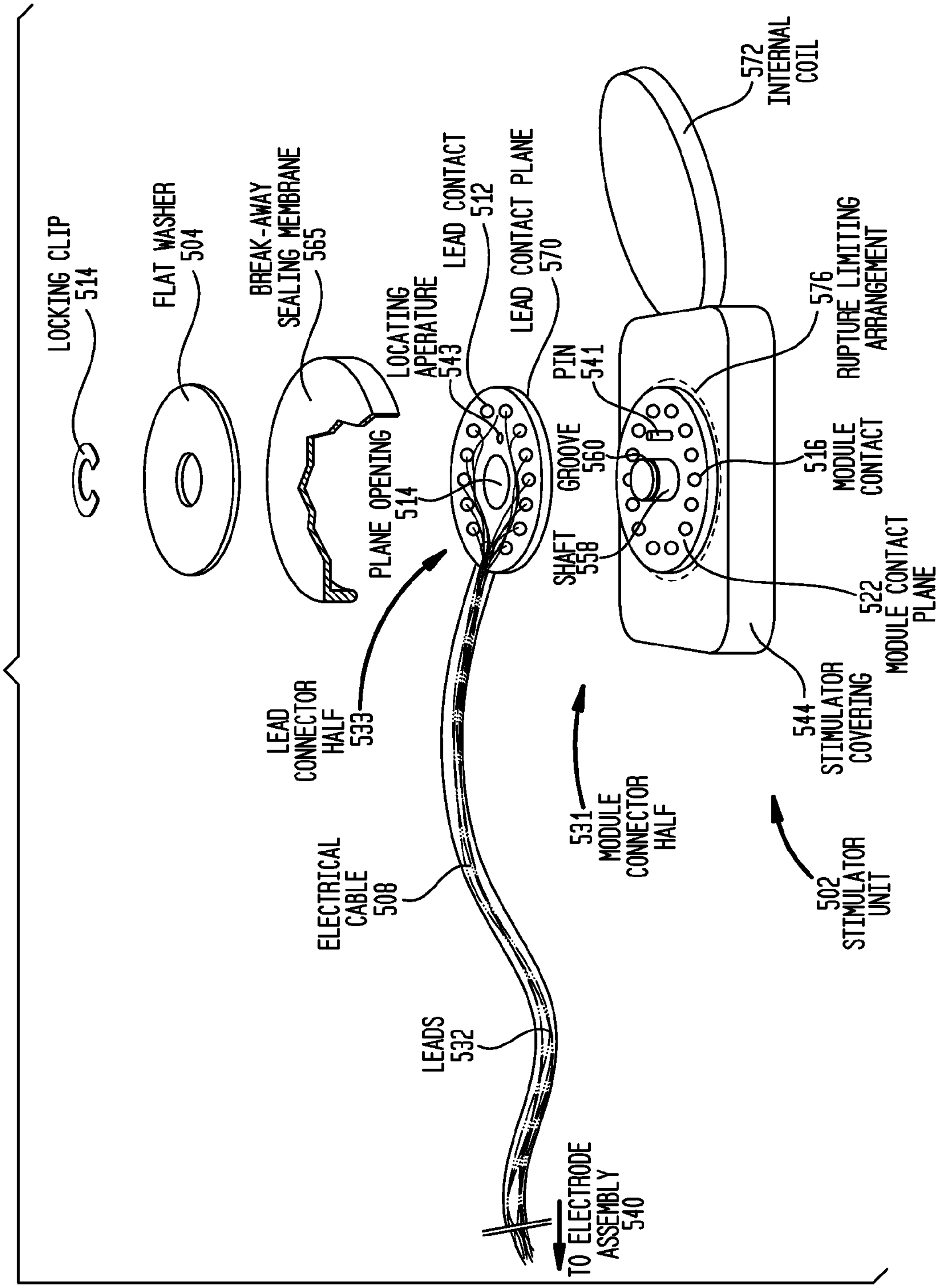
FIG. 5B is an exploded view of the electrical connector illustrated in FIG. 5A.

FIG. 5B illustrates an exploded view of an electrical connector 510 configured to electrically connect electrode assembly 540 with stimulator unit 502. As illustrated in FIG. 5B, electrical connector 510 comprises two connector halves. A first connector half of electrical connector 510, referred to herein as module connector half 531, is electrically coupled to stimulator unit 502. Module connector half 531 comprises a module contact plane 522 having one or more module contacts 516 disposed therein or thereon. In certain circumstances, module contact plane 522 may comprise a feed through insulator configured to electrically isolate module contacts 516 from one another. As discussed below in more detail, module contact plane 522 further includes an elongate shaft 558 distally extending there from. Shaft 558 has disposed thereon a groove 560. Shaft 558 and groove 560 are described below.

Module contacts 516 may each be connected to other components of stimulator unit 502 via one or more contact wires (not shown). Such contact wires are configured for the bidirectional transfer of signals between module contacts 516 and stimulator unit 502. It should be appreciated that any number of the contact wires may be used.

As shown in FIG. 5B, the second connector half of electrical connector 510, referred to herein as a lead connector half 533, comprises a lead contact plane 570 electrically coupled to electrode assembly 540. Lead contact plane 570 includes one or more lead contacts 512 positioned therein or thereon. As described below, lead contacts 512 are configured to be electrically coupled to module contacts 516 of first contact plane 552. Also as described below, lead contact plane 570 comprises an opening, referred to as plane opening 514, extending there through.

Connected to each lead contact 512 are one or more leads 532. Leads 532 extend from lead contacts 512 through an electrical cable 508 to electrodes of electrode assembly 540. In embodiments of FIG. 5B, a single lead 532 extends between a single plug lead contact 512 and a corresponding electrode. Electrical cable 508 comprises a flexible cable having one or more lumens there through. Leads 532 extend through these lumens.

In the embodiments illustrated in FIG. 5B, module and lead contact planes 522, 570 are configured to mate with each other to electrically connect stimulator unit 502 and electrode assembly 540. The mating of module and lead contact planes 552, 570 refers to the positioning of the contact planes coaxially adjacent one another so that electrical connections may be formed between one or more module contacts 516 and one or more lead contacts 512, respectively. More specifically, in the illustrated embodiment, module and lead contact planes 522, 570 are mated with one another by placing plane opening 514 over shaft 558, and sliding lead contact plane 570 over shaft 558 until lead contact plane 570 is coaxially adjacent module contact plane 522. Once module and lead contact planes 552, 570 are positioned coaxially adjacent one another, contacts planes 522 and 570 may be rotated with respect to one another so that module contacts 516 of module contact plane 522 may be electrically coupled to lead contacts 512 of lead contact plane 570, respectively.

In certain embodiments, planes 570 and 522 may comprise an arrangement of alignment elements to facilitate proper alignment of contacts 516 with corresponding contacts 512. It would be appreciated that a number of different types of alignment arrangements may be implemented in embodiments of the present invention. FIG. 5B illustrates one exemplary alignment arrangement comprising a spigot or locating pin 541 extending from the surface of module contact plane 522. The alignment arrangement of FIG. 5B further comprises a locating aperture 543 configured to receive pin 541 therein. When pin 541 is positioned in aperture 543, module contacts 516 are aligned with corresponding lead contacts 512. As noted, other known methods to maintain alignment between mating parts may be equally employed to effect alignment of planes 522 and 570. Exemplary alignment arrangements may also prevent undesired rotation of planes 522 and 570 with respect to one another.

FIG. 5B illustrates embodiments in which the alignment arrangement comprises one element on each of planes 522 and 570. It would be appreciated that an alignment arrangement may comprise other numbers disposed on each plane 522 and 570.

When contacts planes 522 and 570 are mated with one another, electrical connector 510 is sealed to maintain the integrity of the electrical connection between contact planes 522, 570. The seal is provided by a break-away sealing membrane 565 that protects at least the electrical connections between contact planes 522, 570. Break-away sealing membrane 565 is substantially similar to the break-away sealing membranes described above. Specifically, membrane 565 is configured to be ruptured so as to allow stimulator unit 502 and electrode assembly 540 to be disconnected from each other with minimal force. In one embodiment, break-away sealing membrane 565 is configured to rupture when subjected to a force having a magnitude that is approximately the same as the magnitude of the force which is necessary to manually disconnect contact plane 570 from contact plane 522 without the presence of the break-away sealing membrane 565. In one specific embodiment, sealing membrane 565 is configured to rupture when subjected to a manual force applied by a surgeon to manually disconnect contact plane 570 from contact plane 522. In these embodiments, a surgeon may slightly twist, pull, or otherwise move electrical cable 508 or lead contact plane 570 so as to cause break-away sealing membrane 565 to rupture In certain applications of the present invention, one or both of electrode assembly 540 and stimulator unit 502 are electrically coupled to their respective contact planes 570, 522 via a flexible element or cable. Such a flexible element is configured to allow a contact plane 570, 522 to be moved within the patient adjacent to, or within, the surgical space without causing movement of its associated component, electrode assembly 540 or stimulator unit 502, respectfully. This permits the in situ physical separation of electrode assembly 540 and stimulator unit without causing translation, rotation or otherwise physically disturbing electrode assembly 540. In some embodiments, the ability to disconnect stimulator unit 502 without disturbing electrode assembly 540 permits the independent explanation of stimulator unit 502 from the recipient while leaving electrode assembly 540 implanted in the cochlea of the recipient. In such embodiments, subsequent connection of a repaired or replacement stimulator unit 502 may be attained by mating contact plane 570 with contact plane 522 and reestablishing break-away sealing membrane 565.

In certain circumstances, contacts planes 522 and 570 are configured to provide a minimum leakage volume there between. In these embodiments, contacts planes 522 and 570 are designed such that if a fluid penetrates break-away sealing membrane 265, the space between the connector halves is sufficiently small that the fluid will not interfere with the electrical connection there between. In certain embodiments, at least one of contacts planes 522 and 570 comprises a gap consuming compliant material configured to substantially fill any space there between, thereby providing the minimum leakage volume.

In certain embodiments, similar break-away sealing membrane 265 discussed above, break-away sealing membrane 565 may comprise a portion of exterior layer 504 having a thickness that is substantially less than the remainder of exterior layer 504. Alternatively, exterior layer 504 may comprise first and second materials, each material having different rupture strengths, and break-away sealing membrane may comprise a portion of exterior layer 504 having lower rupture strength.

Additionally, break-away sealing membrane 565 may have integrated therein, or be adjacent to, a mechanical weakness, illustrated in FIG. 5A as line of weakness 552. In such embodiments, break-away sealing membrane 565 may be configured to rupture at line of weakness 552. As described above with reference to FIG. 2A, the mechanical weakness may comprise a score, notch, or other intentionally created weakness.

In certain circumstances, exterior layer 504 may include a rupture limiting arrangement 576 configured to prevent any rupture in break-away sealing membrane 565 from spreading to stimulator covering 544. As shown in FIG. 5B, rupture limiting arrangement 576 may be provided by including metal members within stimulator covering 544. The metal members may be configured to act as internal cutting members upon the application of a force to break-away sealing membrane 565. In a specific embodiment, the metal members comprise a pair of adjacent yet physically spaced metal members each having a sharp portion. In such specific embodiments, upon the application of a force, the sharp portions of the spaced members result in a rupture occurring substantially between the metal members. In other embodiments, rupture limiting arrangement 576 may comprise an additional mechanical weakness.

In certain embodiments, break-away sealing membrane 565 may be configured to have sufficient strength to retain module and lead contact planes 522, 570 in position with respect to each other. In other embodiments, plane opening 514 may be configured to frictionally engage shaft 558 to prevent movement of lead contact plane 570 with respect to module contact plane 522.

In still other embodiments, a locking arrangement may be provided to retain lead contact plane 570 in position with respect to module contact plane 522. One exemplary locking arrangement is shown as locking clip 514 in FIG. 5B. As noted above, shaft 558 comprises a groove 560 therein and locking clip 514 may be configured to engage groove 560 to exert a force on lead contact plane 570. In such an embodiment, the force on lead contact plane 570 would substantially prevent lead contact plane 570 from moving with respect to module contact plane 522. In specific embodiments of the present invention, a washer 504 may be further provided to spread the pressure from locking clip 514.

In the embodiments of FIG. 5B, module and lead contact planes 522, 570 each have a substantially cylindrical shape. However, it would be appreciated that in alternative embodiments of the present invention module and lead contact planes 522, 570 may have square, rectangular or other shapes.

Figure 6A:
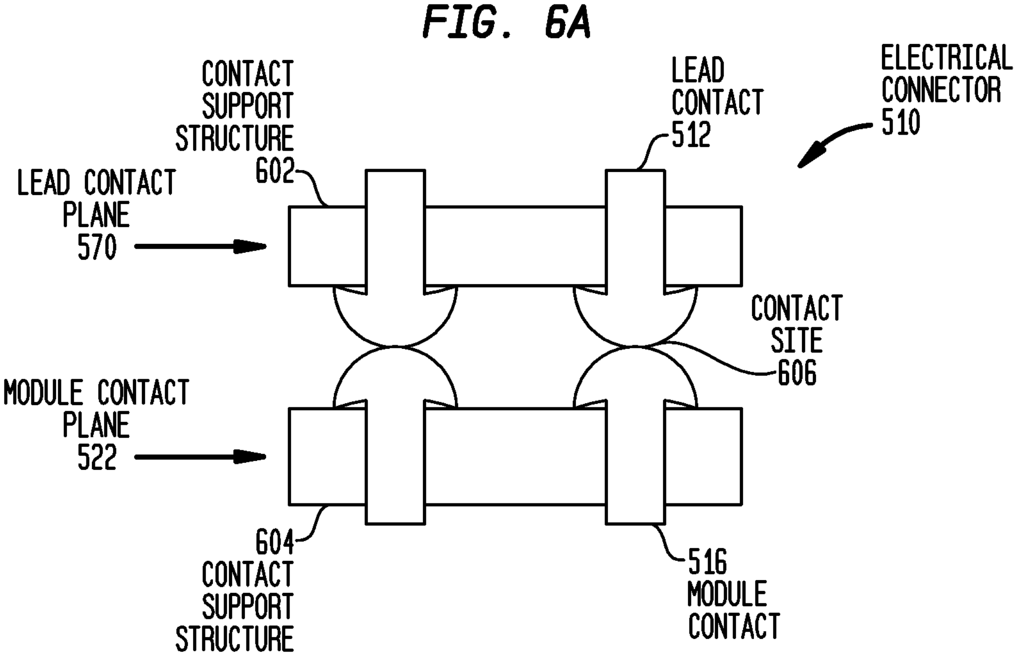
FIG. 6A is a cross-sectional view of a portion of the electrical connector of FIGS. 5A and 5B.

FIG. 6A is a cross-sectional view of a portion of lead and module contact planes 570, 522 of electrical connector 510 of FIGS. 5A and 5B. In the illustrative embodiment of FIG. 6A, lead contact plane 570 comprises a contact support structure 602 in which a plurality of lead contacts 512 are disposed. Similarly, module contact plane 522 comprises a contact support structure 604 in which a plurality of module contacts 526 are disposed. Support structures 602, 604 comprise insulative material so as to electrically isolate adjacent contacts 512, 516, respectively, from one another. In certain embodiments, support structures 602, 604 each comprise a feed through insulator.

For ease of illustration, only two of each of the lead and module contacts 512, 516 are illustrated in FIG. 6A. However, it would be appreciated that each support structure 602, 604 may have disposed therein any number of contacts.

In the embodiment illustrated in FIG. 6A, module and lead contact planes 522 and 570 are mated such that module contacts 516 abut corresponding lead contacts 512. The abutting contacts form electrical connections between the connector halves. However, a surface boundary exists at the location where contacts 516, 512, abut one another, shown as contact sites 606. Such surface boundaries may affect the reliability of the connector if, for example, lead and module contacts 512, 516 move relative to one another so as degrade the electrical connections.

Certain embodiments of the present invention, described below with reference to FIGS. 6B-15B, are directed to connector halves in which the likelihood of such degradation of the electrical connection is reduced. In such embodiments, the two halves of a connector are electrically connected to one another via contiguous unitary contacts.

Figure 6B:
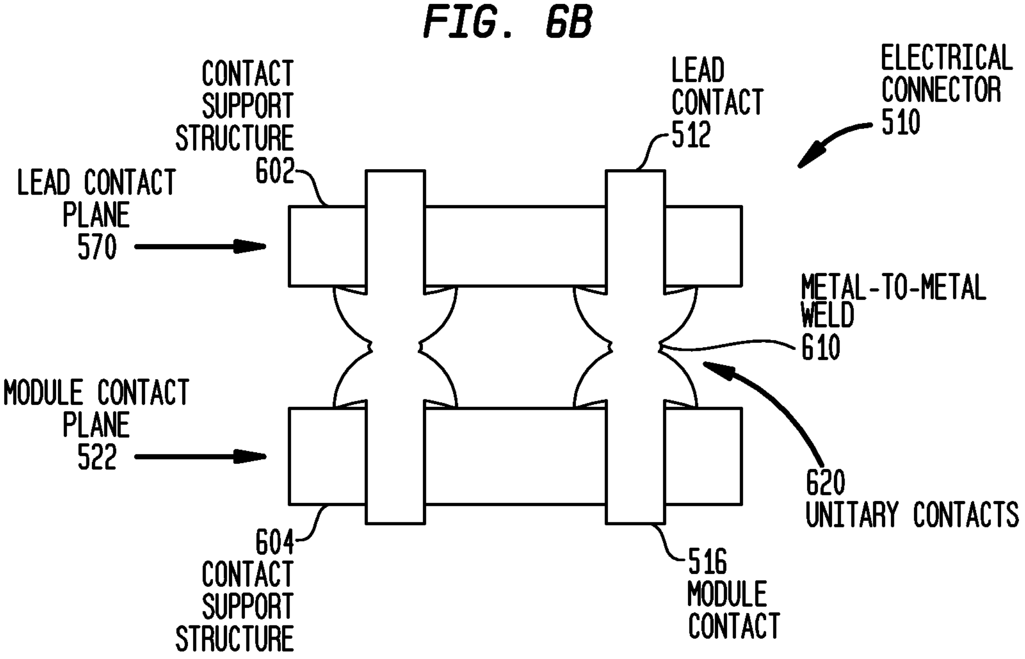
FIG. 6B is a cross-sectional view of a portion of the electrical connector of FIGS. 5A and 5B having a contiguous unitary contact electrically connecting the connector halves, in accordance with an embodiment of the present invention.

FIG. 6B illustrates the portion of electrical connector 510 of FIG. 6A in which the corresponding contacts are fused together via metal-to-metal welds 610 form exemplary unitary contacts 620. As such, the unitary contacts comprise contiguous conductive pathways from which the surface boundaries at contact sites 606 (FIG. 6A) have been eliminated. In embodiments of the present invention, lead and module contacts 512 and 516 are formed from platinum and metal-to-metal welds 610 are platinum metal-to-metal welds.

In certain embodiments, metal-to-metal welds 610 in may be formed during the manufacture of electrical connector 510. Alternatively, metal-to-metal welds 610 may be formed in situ. That is, metal-to-metal welds 610 may be formed after implantation of one or both of contact planes 522 and 570 into the recipient. Exemplary methods for forming metal-to-metal welds are described in greater detail below.

Figure 7:
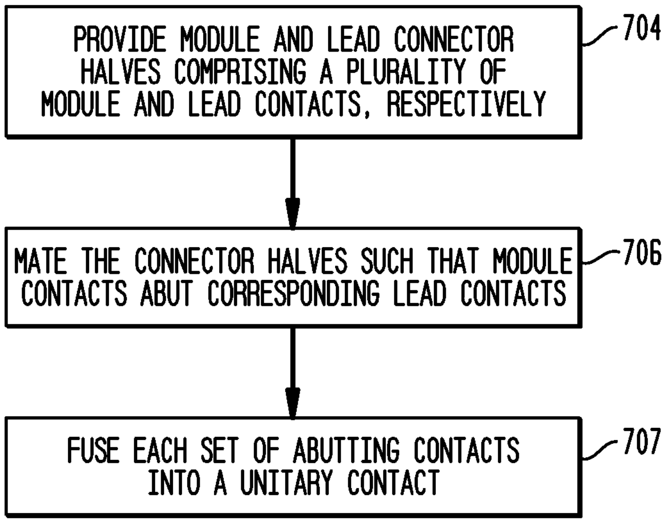
FIG. 7 is a flowchart illustrating the relevant operations performed in electrically connecting two connector halves, in accordance with embodiments of the present invention.

FIG. 7 is a flowchart illustrating the manufacture of an implantable cochlear implant comprises a stimulator unit electrically connected to an electrode assembly. The process begins at block 704 where module and lead connector halves are provided. The module connector half is electrically connected to the stimulator unit and comprises a plurality of module contacts. Furthermore, the lead connector half is electrically connected to the electrode assembly, and comprises a plurality of lead contacts. At block 706, the module and lead connector halves are mated with one another such that each of the module contacts physically abut a corresponding lead contact. At block 707, each set of abutting module and lead contacts are fused into unitary contacts via metal-to-metal welds.

Figure 8A:
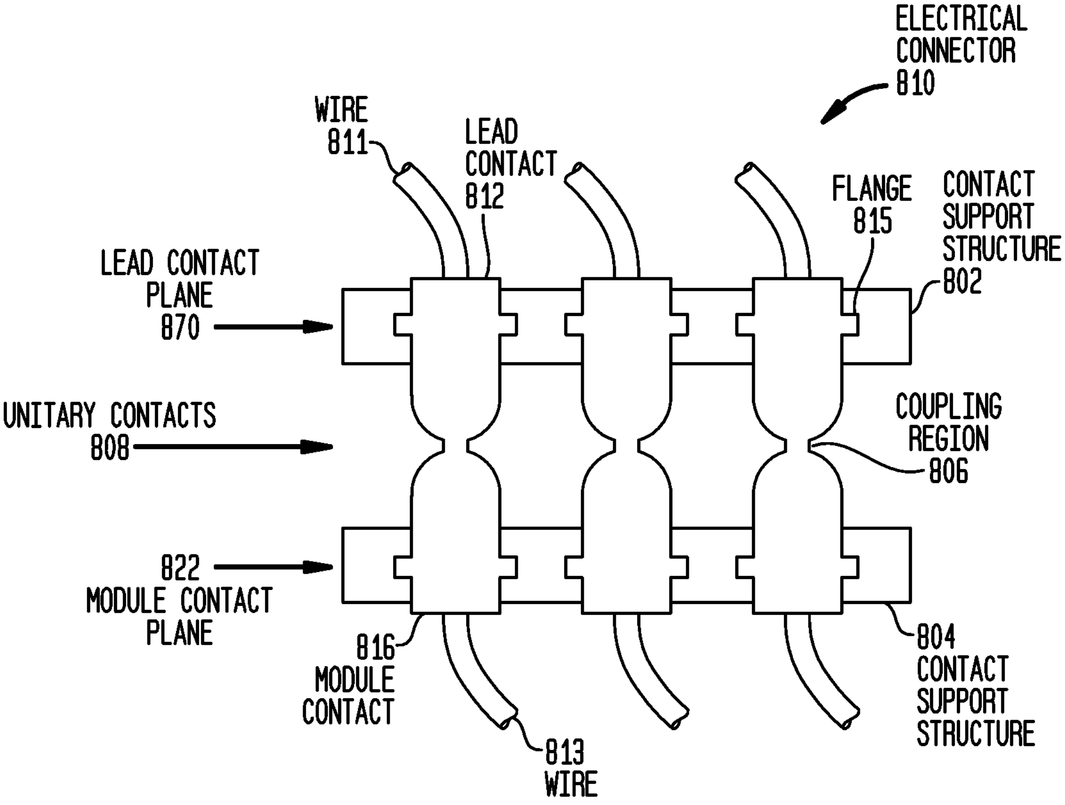
FIG. 8A is a cross-sectional view of a portion of an electrical connector, in accordance with embodiments of the present invention.

In the embodiment FIG. 8A is a cross-sectional view of a portion of an electrical connector 810 in accordance with further embodiments of the present invention. As shown, electrical connector 810 comprises a lead contact plane 870 and module contact plane 822. Lead and module contact planes 870, 822 are substantially similar to planes 570 and 522, respectively, described above.

As shown, electrical connector 810 comprises a plurality of contiguous unitary contacts 808 extending between planes 822, 870. In the embodiments of FIG. 8A, each contiguous unitary contact 808 is manufactured as an integrated, single piece structure, comprising a lead contact 812 connected to a module contact 816 via coupling region 806. Each lead contact 812 is coupled to a wire 811 which extends from the lead contact to one or more electrodes of an electrode assembly. Similarly, each module contact 816 is coupled to a wire 813 which extends from module contact 816 to a stimulator unit. Furthermore, coupling region 806 has a cross-sectional area which is small relative to the cross-sectional areas of lead and module contact 812 and 816. However, it would be appreciated that in alternative embodiments coupling region may take different shapes and sizes.

Figure 8B:
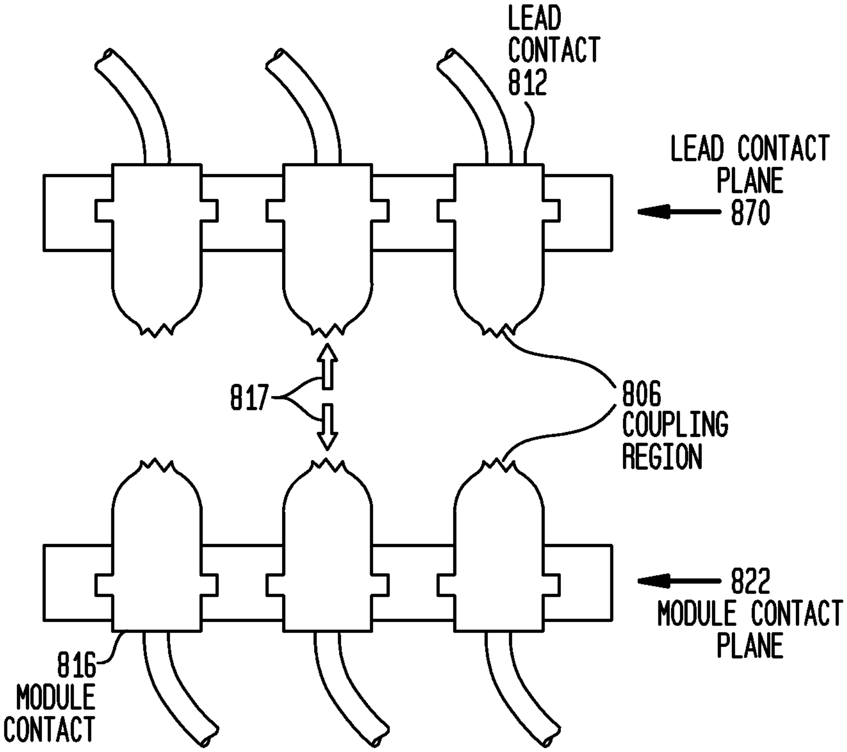
FIG. 8B is a cross-sectional view of a portion of the electrical connector of FIG. 8A illustrating the severing of a contiguous unitary contact, in accordance with embodiments of the present invention.

In the embodiments of FIG. 8A, unitary contacts 808 are readily severable. That is, the contiguous unitary contacts are configured to be severed or broken through the application of a minimal amount of manual force. FIG. 8B illustrates the application of a manual force which pulls planes 870 and 822 away from each other along an axis substantially perpendicular to the lead and contact planes, shown by arrows 817. As shown, upon application of such a force, unitary contacts 808 are configured to sever at coupling region 806. Each unitary contact 808 severs at coupling regions 806 as a result of any number of factors including, but not limited to, the relatively small cross-sectional area of coupling regions 806, the shape and length of coupling regions 806, etc.

In the specific embodiments of FIG. 8A, contiguous unitary contacts 808 also comprises a plurality of flanges 815 that serve to securely fasten lead and module contacts 812, 816 into support structures 802, 804, respectively. As shown, flanges 815 comprise portions of contacts 812, 816 which extend laterally from the main body of the contacts into the support structures 802, 804. Therefore, upon application of a force to unitary contacts 808, flanges 815 retain the contacts within the support structure.

Figure 8C:
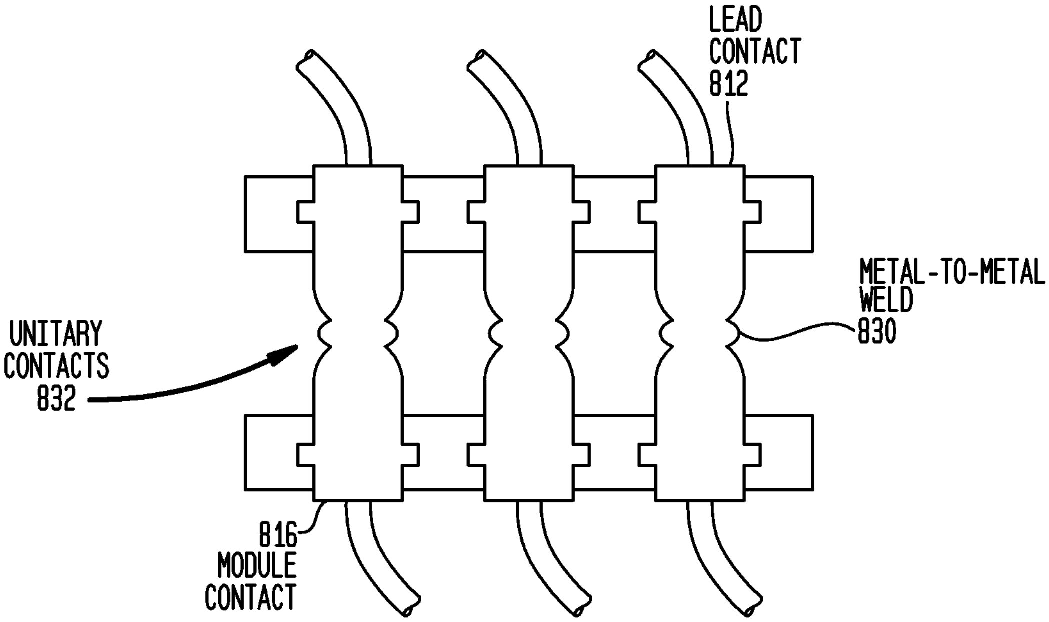
FIG. 8C is a cross-sectional view of a portion of the electrical connector of FIGS. 8A and 8B illustrating contiguous unitary contacts formed through the use of metal-to-metal welds, in accordance with embodiments of the invention.

As noted, contiguous unitary contacts 808 shown in FIGS. 8A and 8B comprise one-piece integrated components formed prior to, or during the manufacture and/or assembly of electrical connector 810. However, as detailed above with reference to FIG. 6B, in alternative embodiments unitary contacts may be formed using metal-to-metal welds. FIG. 8C is a cross-sectional view of a portion of electrical connector 810 in which metal-to-metal welds 830 are used to form unitary contacts 808. Similar to the embodiments of FIGS. 8A and 8B, metal-to-metal welds 830 may be formed such that unitary contacts 832 are readily severable by the application of minimal force thereto. Once severed, metal-to-metal welds 812 may be repeatedly severed and re-formed over the life of the electrical connector.

Figure 9A:
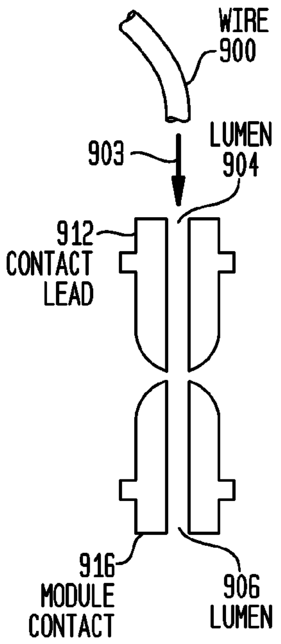
FIG. 9A is a cross-sectional view of lead and module contacts configured to receive a wire, in accordance with embodiments of the present invention.
Figure 9B:
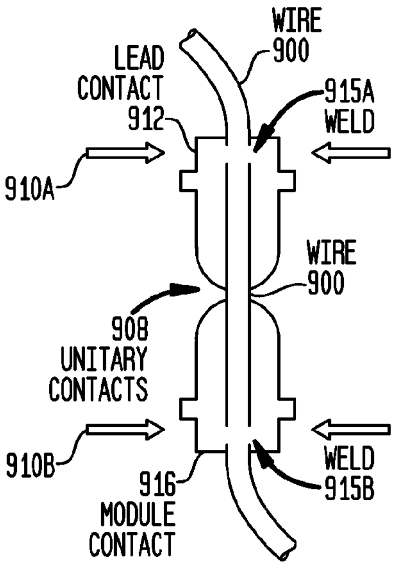
FIG. 9B is a cross-sectional view of the lead and module contacts of FIG. 9A having a wire passing there through, in accordance with embodiments of the present invention.
Figure 9C:
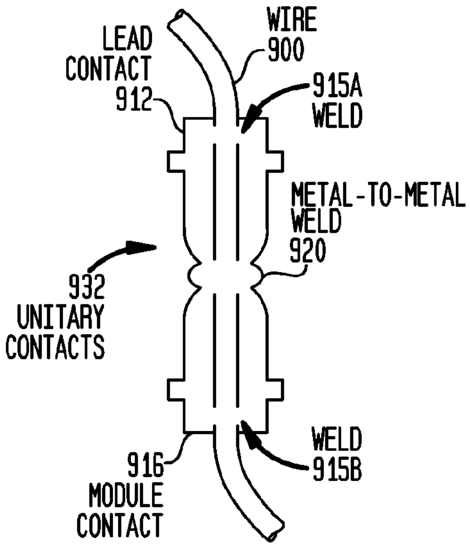
FIG. 9C is a cross-sectional view of the lead and module contacts of FIG. 9B having a metal-to-metal weld formed between the contacts, in accordance with embodiments of the present invention.

A contiguous unitary contact in accordance with embodiments of the present invention may be formed using several different techniques or processes beyond those described above. FIGS. 9A-9C illustrate a unitary contact 908 formed using one such alternative technique. Specifically, FIG. 9A is a cross-sectional view of a lead contact 912 and a module contact 916. Lead and module contacts 912, 916 each have a lumen extending through a longitudinal axis thereof. Specifically, lumen 904 extends through lead contact 912, while lumen 906 extends through module contact 916. As shown in FIG. 9A, when contacts 912 and 916 are positioned so as the ends of the contacts abut, or are substantially adjacent, lumens 904 and 906 are substantially collinear with one another.

After positioning the ends of lead and module contacts 912 and 916 adjacent one another, a wire 900 is passed through lumens 904 and 906, as illustrated by arrow 903 in FIG. 9A. A first end of wire 900 is connected to a stimulator unit, while a second end of the wire is connected to an electrode assembly. In certain embodiments, after wire 900 has been passed through lead and module contacts 912 and 916, wire 900 is welded to each of lead contact 912 and module contact 916 at the base of the contacts, shown by arrows 910.

Wire 900 may be welded to lead and module contacts 912 and 916 using several different techniques. For example, in one embodiment the welding may occur by selectively heating wire 900 contacts 912, 916 such that a first portion of wire 900 and a portion of each of the contacts 912 melt and subsequently fuse with one another to form welds 915. In an alternative embodiment, welds 915 are formed via cold welding.

Similar to the embodiments described above, after forming unitary contacts 908, the contacts may be incorporated into an electrical connector In such embodiments, unitary contacts 908 may be physically severed through the application of, for example, a manual force. However, in contrast to the embodiments described above, in the embodiments of FIG. 9B, unitary contacts 908 are not severed at welds 915. Rather, wire 900 of contiguous unitary contacts 908 severs at the location where the wire exits lead contact 912 and enters module contact 916. That is, wire 900 severs at the junction of the ends of contacts 912 and 916.

Following the severing of contiguous unitary contact, a new unitary contact 932 may be formed as shown in FIG. 9C. Specifically, lead contact 912 and module contact 916 are repositioned such that the ends of the contacts abut one another. When the end of lead contact 912 abuts the end of module contact 916, the ends of the contacts are fused together via a metal-to-metal weld 920. Because the ends of fused in this manner, the surface boundaries between contacts 912 and 916 are eliminated.

In the embodiment illustrated in FIGS. 9A and 9B, wire 900 is a platinum conductor. However, it would be appreciated that wire 900 may be formed from a number of different conductive materials. Additionally, it would be appreciated that wire 900 may comprise a single-strand wire or a multiple-strand wire, and may be flexible, non-flexible, or malleable, so long as wire 900 is also readily severable through the application of a minimal amount of force.

Figure 10:
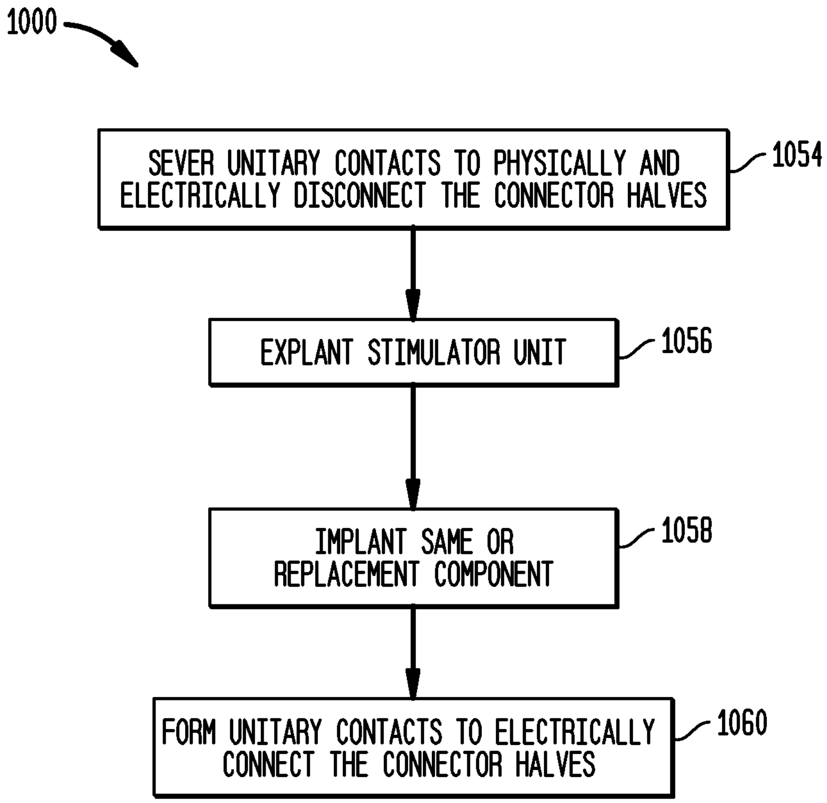
FIG. 10 is a flowchart illustrating the relevant operations performed during the in situ adjustment of an implanted stimulator unit electrically connected to an electrode assembly, in accordance with embodiments of the present invention.

FIG. 10 is a flowchart illustrating an exemplary method 1000 for replacing and/or adjusting an implanted stimulator electrically connected to an implanted electrode assembly via an electrical connector of the present invention. As described above, the electrical connector comprises module and lead connector halves each comprising a plurality of module and lead contacts, respectively. Method 1000 begins at block 1054 where a surgeon manually severs the contiguous unitary contacts of the electrical connector to physically and electrically separate the connector halves. After severing the unitary contacts, at block 1056 the stimulator unit may be explanted without disturbing the implanted location of the electrode assembly within the cochlea.

At block 1058, the explanted stimulator unit, or a replacement stimulator unit, is implanted in the recipient. In embodiments in which a replacement stimulator unit is to be implanted, the replacement stimulator unit is electrically coupled to a module connector half which is configured to mate with the lead connector half connected to the implanted electrode assembly. At block 1060, the newly implanted stimulator unit is electrically connected to the electrode assembly. Specifically, the module and lead connector halves are mated as described above, and in situ metal-to-metal welds fuse the abutting contacts into unitary contacts.

Figure 11:
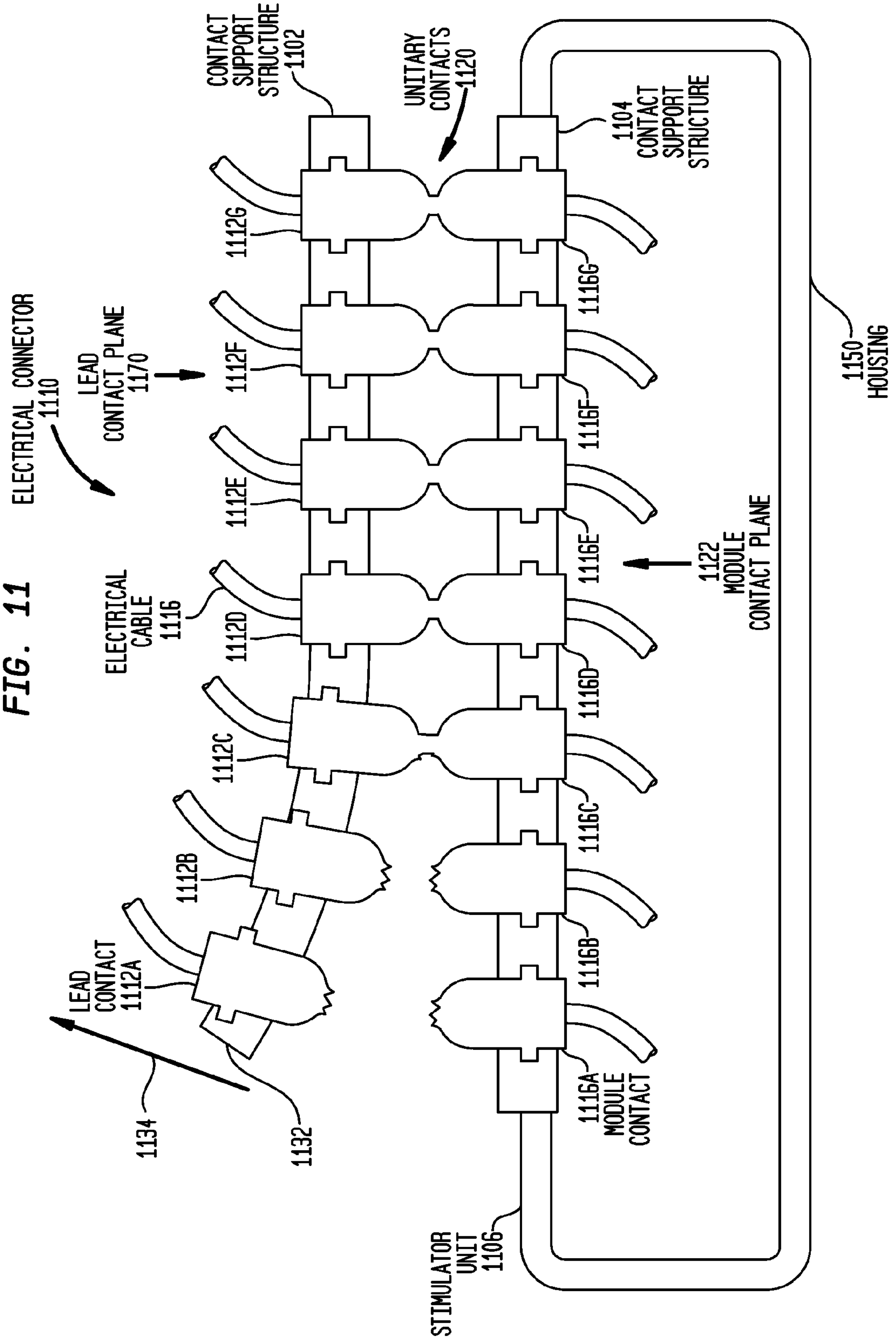
FIG. 11 is a cross-sectional view of two electrical connector halves partially separated, in accordance with another embodiment of the invention.

FIG. 8B above illustrates one exemplary method for severing unitary contacts of the present invention through the application of a force which pulls the module and lead planes away from each other along an axis which is substantially perpendicular to the surface of the planes FIG. 11 illustrates alternative embodiments for severing unitary contacts.

FIG. 11 illustrates an electrical connector 1110 connecting a stimulator unit 1106 to an electrode assembly (not shown). Similar to electrical connector 510 described above, electrical connector 1110 comprises lead and module contact planes 1170 and 1122 electrically connected by unitary contacts 1120. Lead contact plane 1170 comprises a contact support structure 1102 in which a plurality of lead contacts 112 are disposed. Similarly, module contact plane 1122 comprises a contact support structure 1104 in which a plurality of module contacts 1116 are disposed. Contact support structure 1102 comprises a flexible material, such as silicone elastomer, while contact support structure 1104 may comprise a relatively rigid ceramic material that is bonded to housing 1150 of stimulator unit 1106.

As noted above, to lead and contact planes 1170 and 1122 are disconnected from one another by severing unitary contacts 1120. In the embodiments of FIG. 11, contiguous unitary contacts 1120 are severed by applying a minimal disconnecting force at an edge 1132 of lead contact plane 1170 in a direction shown by arrow 1134. As indicated by arrow 1134, the disconnecting force is applied in a direction away from, but not entirely orthogonal to, module contact plane 11122. It would be appreciated that the force location and direction shown in FIG. 11 are merely illustrative and that forces applied at other locations and in other directions may also sever contiguous unitary contacts 1120.

In the embodiment illustrated in FIG. 11, contact support structure 1102 is sufficiently flexible such that when the disconnecting force is applied at edge 1103, contact support structure 1102 will progressively flex so that unitary contacts 1120 are individually and sequentially severed. Because contact support structure 1102 allows individual severing of contiguous unitary contacts 1120, the amount of force required to disconnect lead and module contact planes 1170 and 1122 is substantially the same as the amount of force required to sever one unitary contact 1120. Thus, the risk of disturbing the location of implanted components, such as the electrode assembly, is further reduced relative to embodiments which utilize simultaneous severing of a plurality of unitary contacts.

As noted above, certain embodiments of the present invention utilize metal-to-metal welds to form contiguous unitary contacts. FIGS. 12A-13B illustrate a first exemplary method of forming metal-to-metal welds in accordance with embodiments of the present invention.

Figure 12A:
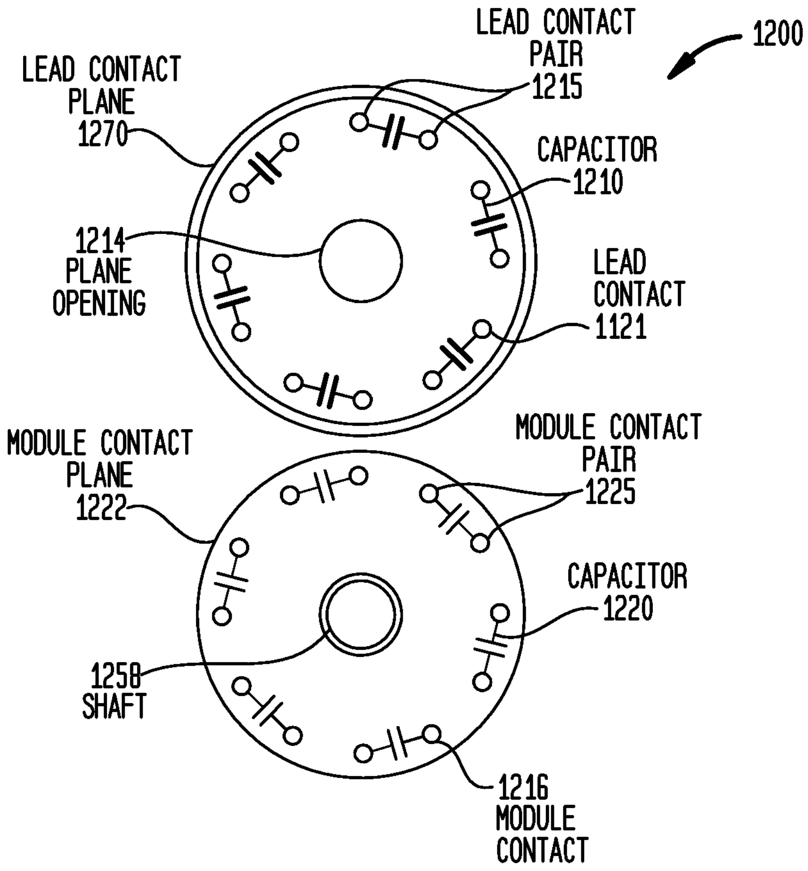
FIG. 12A is a plan view of lead and module contact planes, in accordance with an embodiment of the present invention.
Figure 12B:
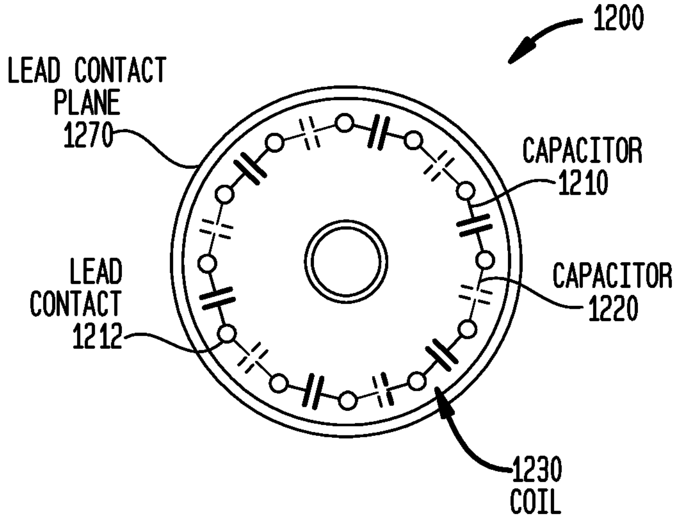
FIG. 12B is a plan view of the lead and module contact planes of FIG. 12A after mating of the contact planes, in accordance with an embodiment of the invention.

Illustrated in FIGS. 12A and 12B are lead and module contact planes 1270 and 1222 of an electrical connector 1200. FIG. 12A illustrates lead and module contact planes 1270, 1222 prior to mating with one another, while FIG. 12B illustrates the lead and module contact planes subsequent to mating.

As shown, lead contact plane 1270 comprises a plurality of lead contacts 1212, while module contact plane 1222 comprises a plurality of module contacts 1216. Lead contact plane 1270 further comprises a plurality of capacitors 1210, each of which is electrically connected between a pair 1215 of lead contacts 1212. Module contact plane 1222 also comprises a plurality of capacitors 1220, each of which is connected between a pair 1225 of module contacts 1216.

Lead and module contact planes 1270 and 1222 are mated with one another by placing plane opening 1214 over shaft 1258, and sliding lead contact plane 1270 over shaft 1258 until lead contact plane 1270 is coaxially adjacent module contact plane 1222. Additionally, lead and module contact planes 1270 and 1222 are mated such that capacitors 1210 of lead contact plane 1270 and capacitors 1220 of module contact plane 1222 are all connected in series, as illustrated in FIG. 12B, to form a single-turn coil 1230. As such, although pairs 1215 and 1225 of contacts are not directly electrically connected to one another, the capacitor structure of coil 1230 forms a continuous electrical pathway between all of the lead and module contacts 1212 and 1216.

In the embodiment illustrated in FIG. 12B, lead and module contact planes 1270 and 1222 are mated such that module contact pairs 1225 are adjacent lead contact pairs 1215. Once lead and module contact planes 1270 and 1222 are mated in this manner, the temporary application of an alternating, high frequency magnetic field induces a current in coil 1230 that melts at least the abutting portions of lead and module contacts 1212 and 1216. Upon cooling of the contacts, the abutting portions fuse together in a substantially surface boundary-free structure, referred to above as a contiguous unitary contact. In some embodiments, the induced current is a high frequency AC current, and the coil 1230 provides a continuous electrical pathway for passing the current to all of the lead and module contacts 1212 and 516.

In embodiments of the present invention, the capacitance value of capacitors 1210 and 1220 is chosen to provide a low impedance electrical pathway for the high frequency current used to heat and fuse the contacts into a weld. However, at the same time, the capacitance provides high impedance to the electrical signals conveyed via the connection in use.

Figure 13A:
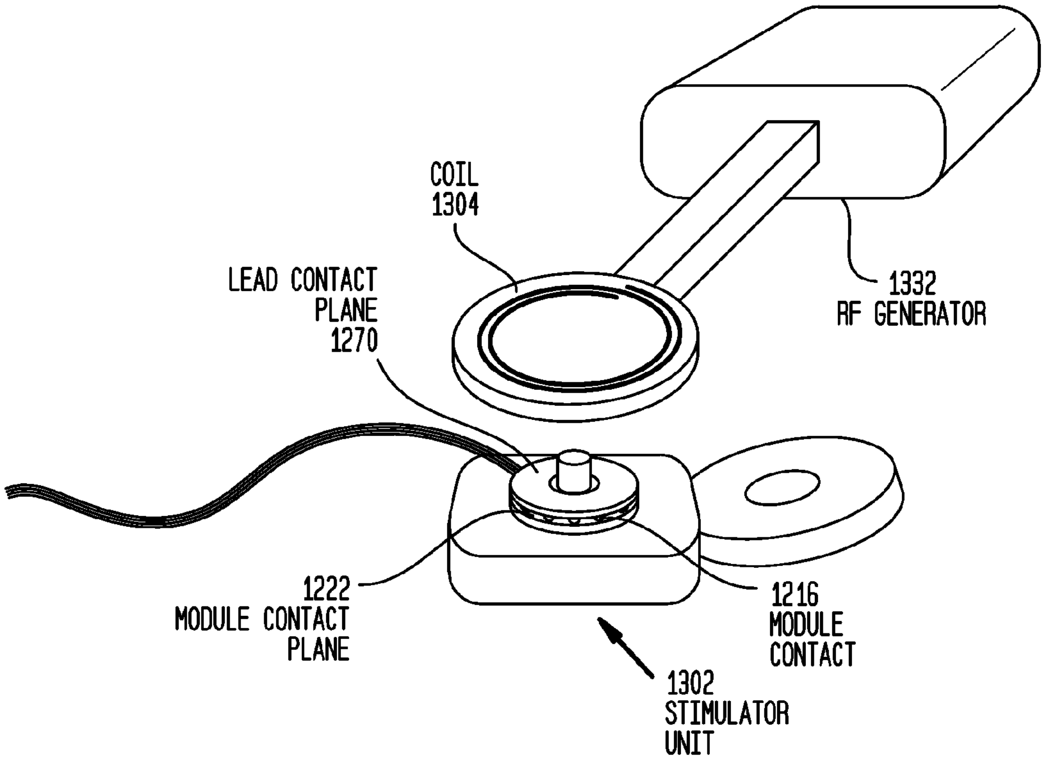
FIG. 13A is a perspective view of a radio frequency (RF) generator and an associated induction coil used in conjunction with the electrical connector of FIGS. 12A and 12B, in accordance with embodiments of the invention.

FIG. 13A is a perspective view of a radio frequency (RF) generator 1302 and an associated induction coil 1304 which may be used to induce an AC circuit in the embodiments of FIGS. 12A and 12B. Specifically, RF generator 1302 causes coil 1304 to emit an alternating, high frequency magnetic field which, when the coil is positioned adjacent to lead contact plane 1270, induces the flow AC across abutting lead and module lead contacts 1212 and 1216. In certain circumstances, RF generator 1302 may be a hand-held, battery operated RF generator.

Figure 13B:
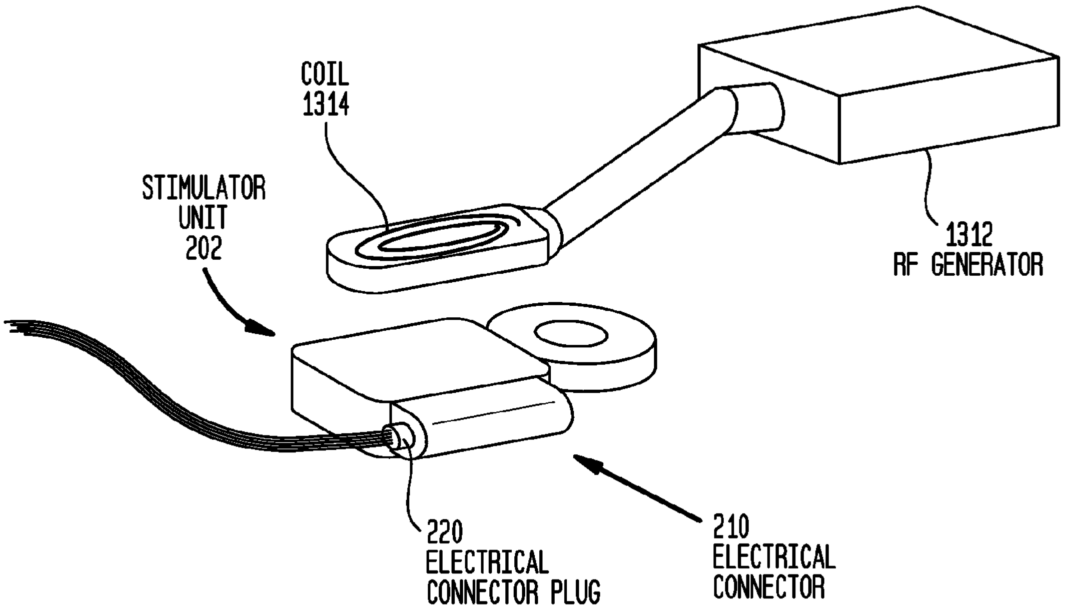
FIG. 13B is a perspective view of a radio frequency (RF) generator and an associated induction coil used in conjunction with an electrical connector of the embodiments illustrated in FIGS. 2A-2E.

FIG. 13B is a perspective view of another RF generator 1312 and an associated induction coil 1314 which may be used to form metal-to-metal welds within electrical connector 210 of FIGS. 2A-2E. Specifically, RF generator 1312 causes 1314 to emit an alternating, high frequency magnetic field which, when the coil is positioned adjacent electrical connector 210, induces a flow of AC current across abutting lead and module contacts 224, 254 (FIG. 2A). This current fuses the abutting portions of lead and module contacts 224 and 254 into metal-to-metal welds.

FIGS. 13A and 13B illustrate embodiments in which a magnetic filed induces an AC current across substantially all of the abutting contacts at substantially the same time. It would be appreciated that in alternative embodiments, a current may be applied to each abutting pair of lead and module lead contacts individually.

Figure 14A:
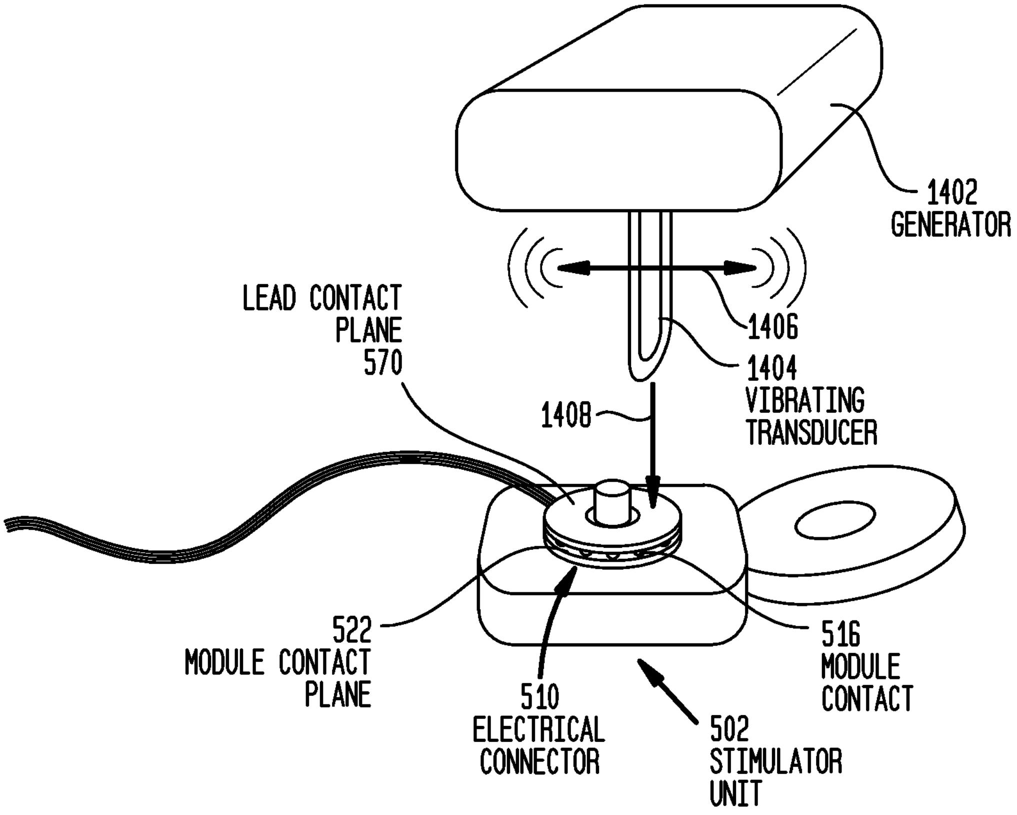
FIG. 14A is a perspective view of a mechanical transducer used to form metal-to-metal welds between abutting lead and module contacts in the electrical connector of the embodiment illustrated in FIGS. 5A and 5B.
Figure 14B:
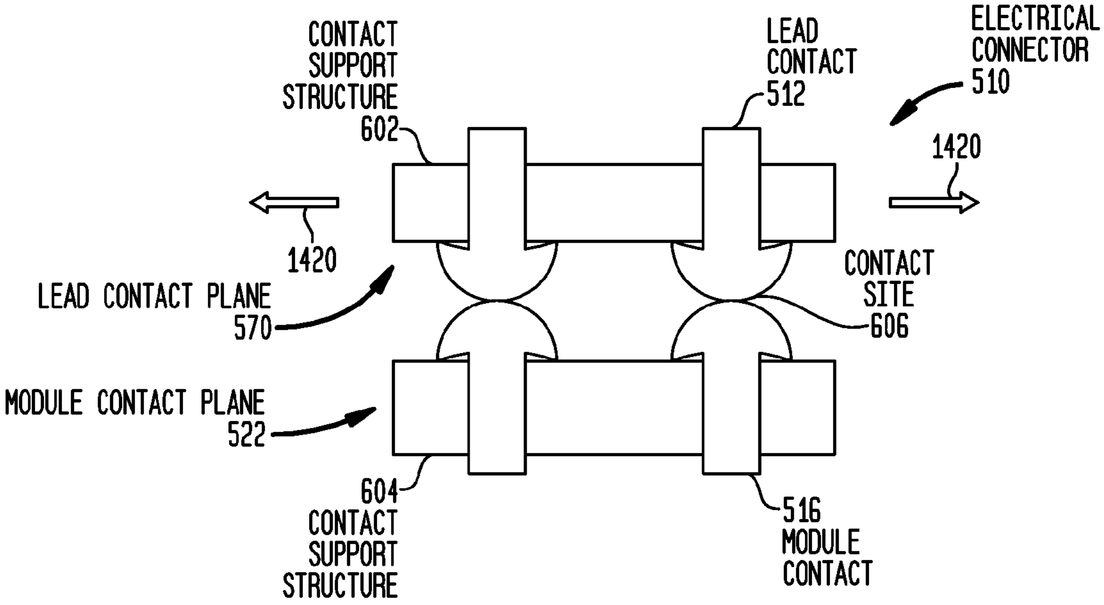
FIG. 14B is a cross-sectional view of a portion of the electrical connector of FIGS. 5A and 5B during vibration by the transducer of FIG. 14A.
Figure 14C:
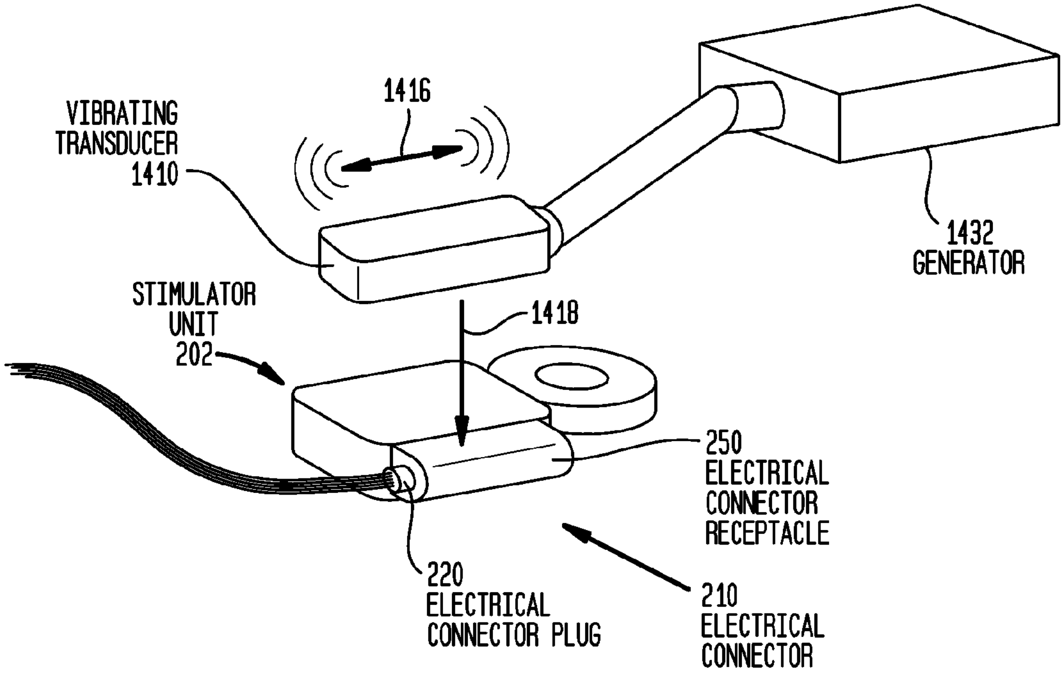
FIG. 14C is a perspective view of a mechanical transducer used to form metal-to-metal welds between abutting lead and module contacts in the electrical connector of the embodiments illustrated in FIGS. 2A-2E.

FIGS. 14A-14C illustrate an alternative method for forming metal-to-metal welds between abutting lead and module contacts. For ease of illustration, the embodiments of FIGS. 14A and 14B will be described with reference to electrical connector 510 of FIGS. 5A-5B. In the illustrative embodiments of FIG. 14A, a high-frequency generator 1402 is connected to a vibrating transducer 1404. Generator 1402 causes transducer 1404 to vibrate back and forth along a lateral axis 1406 which, when the transducer is operationally positioned adjacent to electrical connector 510, is substantially parallel to planes 522, 570. In certain embodiments of the present invention, generator 1402 causes vibrating transducer 1404 to vibrate at a frequency of approximately 50-500 kHz. In specific such embodiments, generator 1402 causes vibrating transducer 1404 to vibrate at a frequency of approximately 100 kHz.

Metal-to-metal welds may be formed in these embodiments by placing vibrating transducer 1404 in physical contact with one of the connector halves of electrical connector 510, such as lead contact plan 570. This physical contact causes high frequency mechanical vibration of lead contact plane 570, illustrated by arrows 1420 in FIG. 14B. Specifically, lead contact plane 570 vibrates relative to module contact plane 522 in a direction with is substantially parallel to a longitudinal axis of module contact plane 522. As lead contact plane 570, the abutting contacts also vibrate such that sufficient frictional heat forms at contact site 606 (FIG. 14B)

to melt the abutting portions of the contacts. Upon removal of the vibration, the melted portions fuse with one another to form contiguous unitary contacts.

In certain embodiments of the present invention, the mass of contact support structure 604 and module contacts 516 may be increased in order to increase the amount of heat generated at contact sites 606 during vibration. Increasing the mass of contact support structure 604 and module contacts 516 increases the magnitude of the relative movement between lead contacts 512 and module contacts 516.

FIG. 14C illustrates the method for forming metal-to-metal welds via vibration with respect electrical connector 210 described above. As shown, a high-frequency generator 1432 is connected to a vibrating transducer 1410. Generator 1432 causes transducer 1410 to vibrate back and forth along a lateral axis 1416. In certain embodiments of the present invention, generator 1432 causes vibrating transducer 1410 to vibrate at a frequency of approximately 50-500 kHz. In specific such embodiments, generator 1432 causes vibrating transducer 1410 to vibrate at a frequency of approximately 100 kHz.

Metal-to-metal welds may be formed in these embodiments by placing vibrating transducer 1410 in physical contact electrical connector receptacle 250 illustrated by arrow 1418. This physical contact causes high frequency mechanical vibration of electrical connector receptacle 250 relative to electrical connector plug 220, thereby generating sufficient frictional heat to melt the abutting portions of the contacts. Upon removal of the vibration, the melted portions fuse with one another to form contiguous unitary contacts.

Figure 15A:
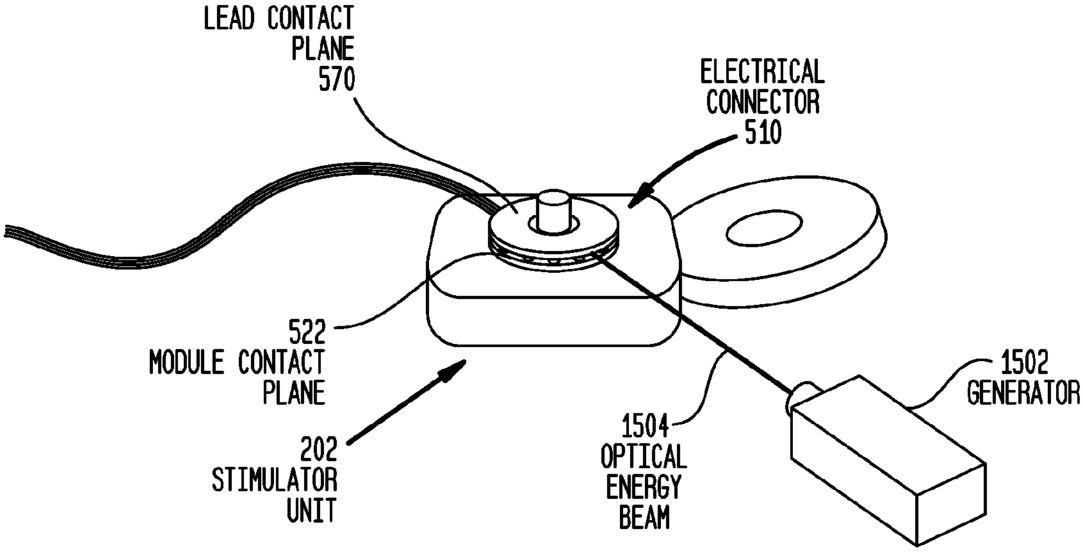
FIG. 15A is a perspective view of a laser beam generator used to form metal-to-metal welds in the electrical connector of embodiments illustrated in FIGS. 5A and 5B.
Figure 15B:
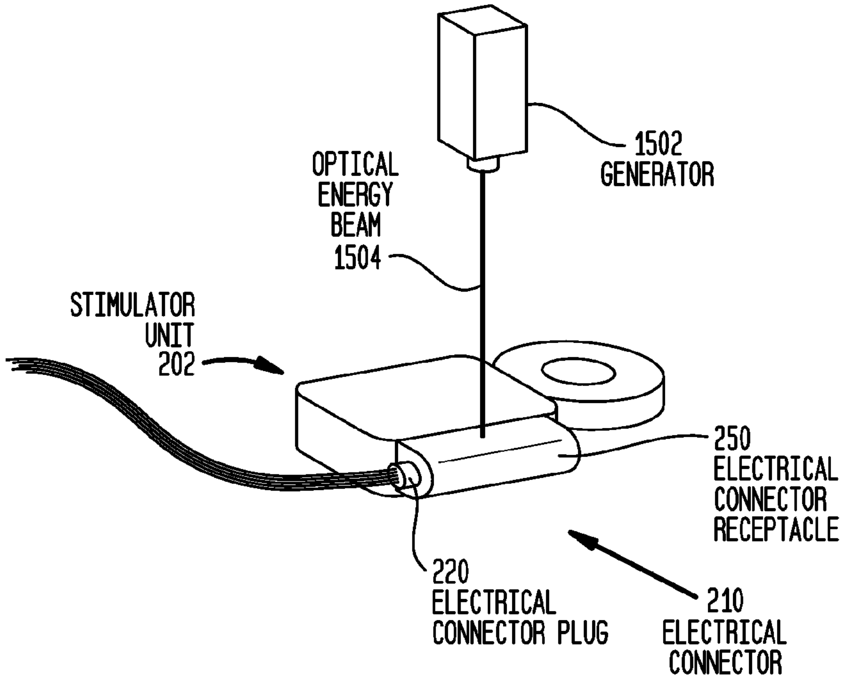
FIG. 15B is a perspective view of a laser beam generator used to form metal-to-metal welds in the electrical connector of embodiments illustrated in FIGS. 2A-2E.

Another exemplary method of forming metal-to-metal welds between abutting lead and module contacts is shown in FIGS. 15A and 15B. For ease of illustration, the embodiments of FIG. 15A will be described with reference to electrical connector 510, while the embodiments of FIG. 15B will be described with reference to electrical connector 210, both described above.

As shown in FIGS. 15A and 15B, an electromagnetic energy beam generator 1502 is positioned proximate to the respective electrical connector 510, 210. As noted above, each connector 510, 210 comprises module and lead connector halves which, when mated with one another, have a series of abutting lead and module contacts. Generator 1502 produces an electromagnetic energy beam 1504 which is delivered through optically accessible portions of electrical connectors 510, 210, to each set of abutting lead and module contacts. Specifically, electromagnetic energy beam 1504 delivers an energy level which is sufficient to melt portions of an abutting lead and module contact. As a result, portions of the abutting contacts fuse with one another to form a contiguous unitary contact. In certain embodiments, electromagnetic energy beam 1504 may be directed to a single pair of abutting contacts at a time, and the fusing may be repeated until all abutting contacts are fused into contiguous unitary contacts. In alternative embodiments, electromagnetic energy beam 1504 may be directed to a plurality, or all of, the abutting contact pairs at one time. In certain embodiments, electromagnetic energy beam 1504 generated by generator 1502 is a narrow beam of infrared electromagnetic energy, such as an infrared laser beam.

In the embodiments of FIGS. 15A and 15B, electrical connectors 510, 210 are each configured to provide a direct or indirect optical pathway between generator 1502 and each pair of abutting lead and module contacts. In some embodiments, one or more components of electrical connectors 510, 210 are transparent, reflective, and/or refractive so as to provide the direct or indirect optical pathway. In some embodiments, the surface reflectivity at the abutting portions of the contacts is reduced in order to assist in the absorption of the optical energy applied using beam 1504.

As noted, various methods for forming contiguous unitary contacts via metal-to-metal welds have been described above. It should be appreciated that these methods are illustrative and that other methods may also be implemented.

It should also be appreciated that the force required to sever contiguous unitary contacts comprising metal-to-metal welds is dependent upon the rate and amount of heat energy delivered, in view of the specific heat, melting temperature, thermal conduction, physical volume, and breaking strength of the material (e.g., metal) fused by the metal-to-metal weld. As such, the amount of force required to sever a contiguous unitary contact formed via a metal-to-metal weld may be altered by controlling the rate and amount of heat energy delivered to abutting lead and module contacts. For example, by reducing the heat produced at the abutting surfaces, the amount of material fused together may be reduced. This may result in a contiguous unitary contact that may be severed by a force that is less than embodiments formed through the use of a greater amount of heat. In one specific example, the momentary delivery of approximately 10 Joules of electrical energy from a capacitor charged to approximately 9 volts by a small battery is sufficient to weld two approximately 100 micrometer diameter platinum metal wires brought together such that approximately 2 grams of mechanical force must be applied in order to break the weld.

As noted above, in certain embodiments of the present invention, contiguous unitary contacts may be severed and repeatedly welded together, as described above, multiple times over the life of a medical device. In such embodiments, platinum having substantially low chemical reactivity is beneficial so that the site of repeated welding of platinum remains substantially free of metal oxide contamination.

In some embodiments of the present invention, an electrical connector may be formed that comprises both a break-away sealing membrane, in accordance with embodiments of the invention, and contiguous unitary contacts, in accordance with embodiments of the invention. In other embodiments of the present invention, an electrical connector may be formed that comprises a break-away sealing membrane, in accordance with embodiments of the invention, but no contiguous unitary contacts. In still other embodiments of the present invention, an electrical connector may be formed that comprises contiguous unitary contacts, in accordance with embodiments of the invention, but not a break-away sealing membrane. Thus, the various above described embodiments of the present invention may be used in a number of different combinations.

This application is related to commonly owned and co-pending U.S. patent application Ser. No. 12/035,940, entitled "AN IMPLANTABLE ELECTRICAL CONNECTOR," filed on Feb. 22, 2008. The content of this application is hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A medical device comprising:

first and second implantable components;

an electrical connector configured to electrically connect the first and second components, comprising:

first and second connector halves electrically coupled to the first and second components, respectively, and one or more first contacts disposed along the first connector half and one or more second contacts disposed along the second connector half, wherein one of the one or more first contacts is fused at a coupling region with a corresponding one of the one or more second contacts to form an integrated, single-piece unitary contact that electrically connects the first and second halves to one another, wherein the unitary contact is readily severable.

2. The device of claim 1, wherein a metal-to-metal weld is located between the one of the one or more first contacts and the corresponding one of the one or more second contacts to join and fuse the two contacts into the integrated, single-piece unitary contact.

3. The device of claim 2, wherein the unitary contact is readily severable at the metal-to-metal weld.

4. The device of claim 1, wherein the unitary contact is readily severable at the coupling region.

5. The device of claim 1, further comprising:

a first lumen extending through the one of the one or more first contacts;

a second lumen extending through the corresponding one of the one or more second contacts, and positioned such that the first and second lumens are substantially collinear; and a wire extending through the first and second lumens to electrically connect the first and second connector halves.

6. The device of claim 5, wherein the wire is welded to one or both of the one of the one or more first contacts and the corresponding one of the one or more second contacts.

7. The device of claim 1, further comprising:

an alignment arrangement configured to ensure alignment of the one of the one or more first contacts on the first connector half with the corresponding one of the one or more second contacts on the second connector half.

8. The device of claim 7, wherein the alignment arrangement comprises:

an aperture in the first connector half; and a pin extending from the second connector half configured to engage the aperture in the first connector half.

9. The device of claim 7, wherein the alignment arrangement comprises a feature on the first connector half configured to frictionally engage a feature on the second connector half.

10. The device of claim 1, wherein the first and second connector halves comprise first and second electrical contact planes, respectively, configured to be positioned co-axially adjacent one another.

11. The device of claim 10, wherein the second contact plane comprises a circumferential disk having an opening there through, and wherein the first contact plane comprises a circumferential disk having a shaft extending there from, and wherein the opening is configured to receive the shaft so that the first and second contact planes are co-axially adjacent one another.

12. The device of claim 11, wherein the shaft has a groove therein, and wherein when the contact planes are co-axially adjacent, the groove is configured to mate with a clip apparatus to retain the contact planes in position with respect to one another.

13. The device of claim 10, wherein the first contact plane is substantially flexible, and wherein the first contact plane may be peeled apart from the second contact plane such that a severing force may be applied to the unitary contact in a sequential manner.

14. The device of claim 1, wherein the readily severable unity contact is rejoinable to reconnect the one of the one or more first contacts with the corresponding one of the one or more second contacts.

15. A connector for electrically connecting first and second implantable components comprising:

first and second connector halves configured to be electrically coupled to the first and second components, respectively, one or more first contacts disposed along the first connector half and one or more second contacts disposed along the second connector half, wherein one of the one or more first contacts is fused at a coupling region with a corresponding one of the one or more second contacts to form an integrally-formed unitary contact that electrically connects the first and second halves to one another, and wherein the unitary contact is readily severable at the coupling region.

16. The connector of claim 15, wherein the one of the one or more first contacts is fused with the corresponding one of the one or more second contacts with a metal-to-metal weld that joins the first and second contacts at the coupling region.

17. The connector of claim 16, wherein the unitary contact is readily severable at the metal-to-metal weld.

18. The connector of claim 15, further comprising:

a first lumen extending through the one of the one or more first contacts;

a second lumen extending through the corresponding one of the one or more second contacts, and positioned such that the first and second lumens are substantially collinear; and a wire extending through the first and second lumens to electrically connect the first and second connector halves.

19. The connector of claim 18, wherein the wire is welded to one or both of the one of the one or more first contacts and the corresponding one of the one or more second contacts.

20. The connector of claim 15, further comprising:

an alignment arrangement configured to ensure alignment of the one of the one or more first contacts on the first connector half with the corresponding one of the one or more second contacts on the second connector half.

21. The connector of claim 15, wherein the first and second connector halves comprise first and second electrical contact planes, respectively, configured to be positioned co-axially adjacent one another.

22. The connector of claim 21, wherein the second contact plane comprises a circumferential disk having an opening there through, and wherein the first contact plane comprises a circumferential disk having a shaft extending there from, and wherein the opening is configured to receive the shaft so that the first and second contact planes are co-axially adjacent one another.

23. The connector of claim 21, wherein the first contact plane is substantially flexible such that that the first contact plane may be peeled apart from the second contact plane so as to sever the unitary contact.

24. The connector of claim 15, wherein the readily severable unity contact is rejoinable to re-connect the one of the one or more first contacts with the corresponding one of the one or more second contacts.

* * * * *